US010497198B2

(12) United States Patent
Pinnow

(10) Patent No.: US 10,497,198 B2
(45) Date of Patent: Dec. 3, 2019

(54) METHOD AND APPARATUS FOR DISCRIMINATING GOLD AND SILVER COINS AND BARS FROM COUNTERFEIT

(71) Applicant: Douglas Arthur Pinnow, Lake Elsinore, CA (US)

(72) Inventor: Douglas Arthur Pinnow, Lake Elsinore, CA (US)

(73) Assignee: Douglas A. Pinnow, Lake Elsinore, CA (US)

( * ) Notice: Subject to any disclaimer, the term of this patent is extended or adjusted under 35 U.S.C. 154(b) by 77 days.

(21) Appl. No.: 15/949,982

(22) Filed: Apr. 10, 2018

(65) Prior Publication Data

US 2018/0300978 A1    Oct. 18, 2018

Related U.S. Application Data

(60) Provisional application No. 62/483,608, filed on Apr. 10, 2017, provisional application No. 62/515,182, filed on Jun. 5, 2017.

(51) Int. Cl.
| | |
|---|---|
| *G01N 9/36* | (2006.01) |
| *G07D 5/00* | (2006.01) |
| *G07D 5/08* | (2006.01) |
| *G07D 5/02* | (2006.01) |
| *G07D 5/04* | (2006.01) |

(52) U.S. Cl.
CPC ............. *G07D 5/08* (2013.01); *G07D 5/02* (2013.01); *G07D 5/04* (2013.01); *G01N 9/36* (2013.01)

(58) Field of Classification Search
CPC .. G07D 5/08; G07D 5/02; G07D 5/00; G07D 5/005; G07D 5/04; G07D 1/00; G07D 3/16; G07D 5/10; G07D 2205/0012; G07D 7/16; G07D 9/04; G07D 1/06; G07D 3/14; G07D 7/20; G01N 2291/0427; G01N 29/045; G01N 29/14; G01N 29/4427; G01N 3/307; G01N 3/56
USPC .............................................. 73/163
See application file for complete search history.

(56) References Cited

U.S. PATENT DOCUMENTS 3,992,938 A * 11/1976 Miller ...................... G07D 5/08
73/163
5,048,662 A * 9/1991 Yamashita ............... G07D 5/00
194/317

(Continued)

*Primary Examiner* — Andre J Allen
(74) *Attorney, Agent, or Firm* — Douglas A. Pinnow

(57) ABSTRACT

Throughout the world, there is growing trend by investors to protect wealth by holding silver and gold coins and bars. Unfortunately, there are also a growing number of counterfeit coins and bars coming into in circulation. This situation cries out for an affordable method that can be used by untrained investors to quickly and reliably discriminate authentic coins and bars from counterfeit ones without causing damage to their coins and bars. The disclosed method fills this need by the use of a combination of conventional and novel designed pieces of equipment for measuring the following three characteristics of a coin; (1) size, (2) weight, and (3) relative terminal velocity on a magnetic slide. The results of these measurements can be used to unambiguously discriminate pure silver and pure gold investment coins and bars from counterfeit ones and can also be helpful in evaluating 22-karat gold coins and pure platinum coins.

26 Claims, 7 Drawing Sheets

(56) References Cited

U.S. PATENT DOCUMENTS

| | | | | |
|---|---|---|---|---|
| 6,761,257 B2* | 7/2004 | Karlsson | ................ | G07D 5/005 194/328 |
| 2002/0034211 A1* | 3/2002 | Baratta | .................. | G01N 25/18 374/45 |
| 2009/0235733 A1* | 9/2009 | Hato | ...................... | G07D 5/005 73/163 |
| 2011/0023596 A1* | 2/2011 | Fortin | ...................... | G07D 5/02 73/163 |
| 2015/0128694 A1* | 5/2015 | Shankman | ............. | G01H 13/00 73/163 |
| 2015/0308983 A1* | 10/2015 | Eames | .................. | G01N 29/12 702/56 |
| 2016/0163141 A1* | 6/2016 | Momose | .................. | G07D 5/08 324/234 |
| 2016/0209364 A1* | 7/2016 | Coffey | .................... | G07D 5/08 |

* cited by examiner

METHOD AND APPARATUS FOR DISCRIMINATING GOLD AND SILVER COINS AND BARS FROM COUNTERFEIT

CROSS REFERENCES TO RELATED APPLICATIONS

This application claims the benefit of U.S. Provisional Patent Application Ser. No. 62/483,608 filed Apr. 10, 2017, titled METHOD AND APPARATUS FOR DISCRIMINATING GOLD AND SILVER COINS AND BARS FROM COUNTERFEIT and U.S. Provisional Patent Application Ser. No. 62/515,182 filed Jun. 5, 2017, also titled METHOD AND APPARATUS FOR DISCRIMINATING GOLD AND SILVER COINS AND BARS FROM COUNTERFEIT the contents of which are hereby incorporated by references herein.

BACKGROUND OF THE INVENTION

1. Field of the Invention

This invention relates to an affordable method that can be used to quickly and reliably discriminate gold and silver coins and bars from counterfeit ones without causing damage to the coins and bars. The disclosed method fills this need by the use of a combination of conventional and novel equipment for measuring the following three characteristics of a coin; (1) size, (2) weight, and (3) relative terminal velocity on a magnetic slide. The results of these measurements can be used to unambiguously discriminate pure (24 karat) gold and pure silver coins and bars from counterfeit ones. The measurement technique can also be applied to the popular 22 karat American Gold Eagle coins and the 22 karat gold Krugerrand coins and pure platinum coins and bars with high but not absolute confidence. It will be shown that any attempt by counterfeiters to produce fake (counterfeit) 24 karat gold or fake pure silver investment coins and bars that satisfy all three of the above characteristics will always result in failure! And this failure will result if a counterfeiter were to alter even a fraction of the precious metal content in a coin by substituting it for non-precious metals or by the use of inserts, laminates, or voids. And although plating external surfaces of counterfeit coins and bars with precious metals may make then visually indistinguishable from authentic coins and bars, this plating would have no appreciable effect on the ability to discriminate them as counterfeit using the method disclosed herein.

2. Description of Related Art

With a growing trend of protecting individual wealth by holding silver and gold investment coins and bars, there is a need for an affordable method that can be used to quickly and reliably discriminate authentic coins and bars from counterfeit ones without causing damage to these coins and bars. This patent disclosure addresses this need.

By way of background, coins struck from precious metal and kept as a store of value or an investment, rather than used in day-to-day commerce are often referred to as "bullion coins". Regulations established in the United Kingdom have gone one step further to define "investment coins" more specifically as coins that have been minted after 1800, have a purity of not less than 90% (0.900 fine) and are, or have been, legal tender in their country of origin. Both of these definitions are used throughout this paper. In particular, this paper is directed to coins that not only conform to the above definition for investment coins but, in most cases, go beyond them by further limiting the gold and silver coins to be at least 99.9% pure (sometimes referred to as a purity of 0.999 fine, as in Table 1, or as 3-nines fine). In this paper, such high purity coins and bars satisfying at least this fineness level will be simply referred to as "pure gold" or "24-karat gold" and/or "pure silver". The same purity levels are also used for gold and silver bars, Two special cases of lower purity (22 karat) gold coins will also be cover be covered in this paper due to the popularity and broad holdings of American Gold Eagle coins and South African gold Krugerrand coins that are made out of 22-karat compositions (that are 22/24=0.9167 pure).

Investment coins and bars are usually available in both gold and silver. In addition, the U.S. American Eagle series is available in gold, silver and platinum, and the Canadian Maple Leaf series is available in gold, silver, platinum, and palladium. See Table 1, below, for additional gold coin producing countries along with their coin weights and purity levels.

This paper will be primarily focused on pure gold and pure silver coins and bars because the methods and procedures disclosed can be used to unambiguously discriminate these types of coin and bars from counterfeit ones. Presently, gold investment coins are being produced in at least the fifteen countries (sovereign nations) shown in Table 1 and silver investment coins are presently being produced in at least 12 countries.

TABLE 1

List of Gold Bullion Coins World Wide

| Country | Name of bullion coin | Purity (Fineness) | Denominations (gold weight) mainly expressed in troy ounces (ozt) | Years of mintage |
|---|---|---|---|---|
| Australia | Gold Nugget | 0.9999 | $1/20$ ozt, $1/10$ ozt, $1/4$ ozt, $1/2$ ozt, 1 ozt, 2 ozt, 10 ozt, 1 kg | 1986-present 1991-present |
| Austria | Vienna Philharmonic | 0.9999 | $1/10$ ozt, $1/4$ ozt, $1/2$ ozt, 1 ozt | 1989-present |
| Canada | Maple Leaf | 0.9999 (.99999 available) | $1/20$ ozt, $1/15$ ozt, $1/10$ ozt, $1/5$ ozt, $1/4$ ozt, $1/2$ ozt, 1 ozt, 100 Kilo | 1979-present |
| China | Gold Panda | 0.999 | $1/20$ ozt, $1/10$ ozt, $1/4$ ozt, $1/2$ ozt, 1 ozt | 1982-present |
| Israel | Jerusalem of Gold Series | 0.9999 | 1 ozt | 2010-present |
| Kazakhstan | Golden Irbis | 0.9999 | $1/10$ ozt, $1/4$ ozt, $1/2$ ozt, 1 ozt | 2009-present |
| Malaysia | Kijang Emas | 0.9999 | $1/4$ ozt, $1/2$ ozt, 1 ozt | 2001-present |

TABLE 1-continued

List of Gold Bullion Coins World Wide

| Country | Name of bullion coin | Purity (Fineness) | Denominations (gold weight) mainly expressed in troy ounces (ozt) | Years of mintage |
| --- | --- | --- | --- | --- |
| Mexico | Libertad | 0.999 | 1/20 ozt, 1/10 ozt, 1/4 ozt, 1/2 ozt, 1 ozt | 1991-present |
| Poland | Orzel bielik | 0.9999 | 1/10 ozt, 1/4 ozt, 1/2 ozt, 1 ozt | 1995-present |
| Russia | George the Victorious | 0.999 | 0.2537 ozt | 2006-present |
| Somalia | Elephant | 0.999 | 1/50 ozt, 1/25 ozt, 1 ozt, 5 ozt | 1999-present |
| South Africa | Krugerrand | 0.9167 | 1/10 ozt, 1/4 ozt, 1/2 ozt, 1 ozt | 1967-present |
| Ukraine | Archangel Michael | 0.9999 | 1/10 ozt, 1/4 ozt, 1/2 ozt, 1 ozt | 2012-present |
| United Kingdom | Britannia | 0.9999 | 1 ozt | 2013-present |
| United States | Gold Eagle | 0.9167 | 1/10 ozt, 1/4 ozt, 1/2 ozt, 1 ozt | 1986-present |
|  | Gold Buffalo | 0.9999 | 1 ozt | 2006-present |

Investment gold coins are typically available in various weights which are usually multiples or fractions of 1 Troy ounce. The most common weight for investment coins throughout the world is one Troy ounce, And, as can be seen in Table 1, most countries that produce investment gold coins produce not only 1-ounce coins, but, ½-ounce, ¼-ounce, and 1/10-ounce coins as well. Larger coins with weights of 1½ ounces and 2-ounces are less common and some bullion coins are produced in very limited quantities that weigh a pound or more. As can be seen in Table 1, the purity of all of these investment gold coins produced throughout the world is 0.999 or better (up to 0.9999), corresponding to 24 karat gold (pure gold), with two important exceptions. The South African Krugerrand and the U.S. Golden American Eagle are both 0.9167 pure, corresponding to 22 karat gold (pure gold is 24 karat while 22 karat gold has a fineness of 22/24=0.9167), In this regard, it is worth noting that South Africa was the first country to introduce gold investment coins in 1967 after the usage of silver was halted in United States in legal-tender coins (dimes, quarters and half dollars) in 1965. Back then, it was commercially more practical for South Africa to use lower purity gold and the United States followed suit in 1982, also with their 22 karat Gold American Eagle coin series, Since testing and validating of these lower purity gold coins is more difficult than with pure gold, it was reasonable for the United States to introduce its 1 Troy ounce Gold Buffalo series in 2006 and thereby align with the 0.999 fineness standard (24 karat) that has been adopted by the remainder of the world's investment coin producing nations (excluding South Africa that continues to produce the lower purity Krugerrand).

With regard to silver investment coins, there are no exceptions to the production of pure silver investment coins with purity of 0.999 or better, including the Silver American Eagle coins first introduced in 1986 and the Silver Krugerrand introduced in 2017.

While the main motivation for the invention disclosed in this paper is to serve the present need of investors to be certain that they are not holding counterfeit precious metal coins and bars that are partially or completely worthless, a secondary purpose is to offer a capability that can be used to rapidly validate gold and silver coins and bars that might be used for commerce in a future world where some or all countries have lost trust in paper currencies printed by central banks. In that regard, it is interesting to note that the various weights of gold coins summarized in Table 1 show a trend to a worldwide standardization based on the 1-Troy ounce gold coin, presently worth approximately $1,300, and various fractional gold coins (½, ¼, and 1/10 ounce) down to the 1/20 Troy ounce coin, presently worth approximately $65, that is produced by Australia, Canada, Mexico. and China. To this mix one can add 1 Troy ounce silver coins, presently worth approximately $20 each and ½ Troy ounce silver coins worth approximately $10. The total value for all of the presently existing gold and silver investment coins worldwide is estimated to be in the range of 500 billion to one Trillion dollars. These coins along with bars and ingots of gold and silver held by all of the central banks worldwide could form a working basis for an inflation proof future monetary system. And such a system would require rapid coin validation at essentially all points of sale to function efficiently.

With so much value stored in investment coins and bars worldwide, it should not be surprising that counterfeiting activity also exists. Yet, none of the legitimate coin producers offers any equipment that can be used to unambiguously discriminate real coins and bars from counterfeit ones. Rather, the situation is as always "Buyer Beware". Consequently, the burden of discriminating authentic gold and silver coins and bars from counterfeit ones falls on the investors who purchase and hold these coins and bars. To assist them, there is a considerable amount of useful information available on the Internet and elsewhere on how to identify counterfeit investment coins and bars. In addition, some commercially produced testing equipment having modest prices and limited capabilities are also available, as will be described next. However, the current reality is that there is no method or equipment available that can provide holders of pure gold and/or silver coins and bars with 100% certainty that they are not holding some counterfeit coins and bars without employing tests damaging to the appearance of their coins and bars or that require a technician to perform validation testing using expensive equipment. Some of the best advice for anyone interested in holding investment coins and bars is to "find and reputable dealer". However, it is believed most investors would prefer a philosophy of "trust but verify" if a practical verification method were made available to them.

Before going on to describe the currently available test equipment and methods for verifying the authenticity of precious metal coins, it should be pointed out that some counterfeit coins can be identified by visual inspection. For example, there is a warning available on the Internet that the letter "O" in the word "ONE" (relating to ONE DOLLAR) on the face of certain counterfeit Silver American Eagle coins is oval in shape rather that circular. In other cases, certain surface details are not as well defined on counterfeit coins as they are on authentic ones. While this type of information is, indeed, helpful, numismatists are well aware that the art of counterfeiting coins has been perfected to the point where, in many cases, they cannot discriminate a rare coin from a counterfeit one even using an optical microscope if the counterfeit coin is made out of the same base metal as the real one. In such cases, only the extremely high power magnification of an expensive electron microscope can be used to provide the necessary discrimination. It is reasonable to assume that similar counterfeiting technology, such as electron discharge machining to reproduce nearly perfect coining dies, is also being used, or will be used, in the production of counterfeit silver and gold bullion coins that are held as investments rather than as a rarity.

In the case of rare coins, the counterfeiters can afford to use whatever base metal is used in the original rare coin because most of the value of such a coin is due to its rarity rather than its metal content. But, this is not the case for most gold and silver investment coins. Their primary value is usually in their metal content rather than rarity.

There are a number of methods and relatively inexpensive tools that individuals can use to determine if a gold or silver coin they are holding or considering for purchase may be counterfeit. One that frequently comes up is a simple magnet test. That is because a magnet can be used to quickly determine if a coin is attracted to it. If so, this immediately implies that the coin has some ferromagnetic content like iron and is therefore counterfeit because neither gold nor silver investment coins or bars are ferromagnetic. However, there are many other metals in the periodic table of elements that are not ferromagnetic and that can be used to make counterfeit investment coins. And there is an unlimited number of metallic alloys (combinations of metal elements) that could not be discriminated by the above magnetic attraction test. So, this simple magnet test by itself is hardly a deterrent to counterfeiters. It only provides marginal protection against purchasing and holding counterfeit coins and bars that are ferromagnetic which represents only a small fraction of the total number of counterfeit coins and bars in circulation.

Another simple, but important, test is to determine if the size of the coin being evaluated matches the values published by its producer. That is because a classic form of counterfeiting is to produce a coin that is, say, 5 to 15% undersized, sometimes even less. An example of this type of counterfeiting is to mill off a small portion of the circumferential edge of an authentic gold coin. In such cases, the removed gold goes to the counterfeiter as profit. But, a measurement of the coin's diameter (or weight) could detect this type of counterfeiting because the diameter would be reduced. In other cases, especially with counterfeit gold coins and bars, they may be oversized so that they will exhibit the correct weight if measured with a precision scale while being made from a metal alloy that may be less dense than gold. Counterfeiters use the strategy of increasing the coin's size or bar's size and, thus, its weight because gold is so dense that it is difficult, but not impossible, to duplicate its high density with most inexpensive alternate metals. In this regard, the density of tungsten comes quite close to that of gold. But, tungsten is not as easy to form as gold and it has a much higher melting point than gold. But, the relatively low price of tungsten (currently, several dollars per ounce) serves to motivate counterfeiters who have developed various methods for inserting tungsten slugs inside of investment coins, bars and ingots that are formed with outer surface layers of pure gold.

Another test that is frequently used to detect counterfeit coins and bars is a weight test. And if the diameter and thickness of the coin being tested (or the outside dimensions of a bar being tested) is also determined, the density of a coin or bar can be calculated by dividing its weight by its volume [volume of a cylindrical coin=$\pi/4$ (diameter)×(thickness) while volume of a rectangular bar=(length)×(width)×(thickness)]. Since density is a basic property of the metal used to make a coin, density is, indeed, a helpful parameter that can help to discriminate pure gold and pure silver from certain counterfeit materials that may have greater or lesser density.

However, most counterfeiters are well aware that it is possible to use inexpensive alloys consisting of a mixture of two or more metals to produce a material that has a density which matches that either of pure silver or pure gold. The methods to make such counterfeit alloys are relatively straightforward. For example, to make a metal alloy that can be used to counterfeit a silver coin, one can combine one or more elements that are more dense but less expensive than silver (such as lead) with less dense elements (such as copper) in proper proportions to produce a metal that precisely matches the density of silver.

The highest accuracy density measurement of a coin can be made by using the method made famous by the ancient scientist, Archimedes, who developed a simple method of calculating the density of an irregular shaped object by weighing it first in air and then weighing it a second time immersed in water. Equipment to perform this type of measurement can be purchased from vendors who advertise their products on the Internet and elsewhere. However, the time required to make such a "wet" measurement is considerably greater than just weighing a coin and measuring its diameter and thickness and comparing these measurements to published values for a coin under examination. Such published values are readily available for all investment coins and bars produced throughout the world.

But even after accurately establishing the density of a coin or bar, it is not possible to make an unambiguous determination if it is made of pure gold or silver even in conjunction with the simple magnetic attraction test, described above. There are simply too many metallic alloys that could be made to have the same density as pure gold or silver that are not attracted to a magnet (non-ferromagnetic).

There are two other tests that should be discussed at this point. One is an electromagnetic test and the other is a test of a coin's acoustic resonant frequency.

The acoustic test is also known as the "ringer" test or the "ping" test. It is an evaluation of the sound that a coin makes when it is dropped onto a solid wood, ceramic, or metal surface or otherwise held only on the tip of a finger while being lightly struck with another coin or some other rigid object. Individuals with a good sense for tones and considerable experience listening to the characteristic ringing (resonant) sounds of different coins and bars can often become skilled at differentiating various coin materials. For example, even most beginners can differentiate the pleasant ringing sound (tone) of a silver coin from the rather dull sound that emanates from a tungsten or lead coin when it is struck. A good analogy to describe why a coin rings when struck would be that of a drummer striking his/her cymbals or bells with a drumstick. After the strike, the cymbal or bell continues to ring (vibrate) with a characteristic sound that can persist for a second or more. Pure silver and 22 karat gold coins both ring rather well, while the ringing of 24 karat gold is more attenuated than 24 karat gold. And it is well known that different sized cymbals and bells made from different materials have different ringing tones (frequencies). By employing this general concept, a commercial product to facilitate the ringing of coins is currently being sold under the product name "The Ringer" (see www.thefish.com on the Internet). It is a simple hand held plastic device that can be used to pinch-grip a coin between the centers of its obverse and reverse surfaces, much like a cymbal is held at its center by a vertical metal shaft. Then when the coin is struck on its rim by a plastic hammer that is formed integral with the plastic ring tester, the coin stays in place but continues to ring (vibrate) after the strike, just like a cymbal. But, even when used by skilled individuals, this test is only a qualitative one. However, in the past several years, several applications (Apps) have been made available to smart cell phone users that can be used to quantify the ringing sound of a coin and thereby further assist them in discriminating against counterfeit ones. Such testing is helpful but not conclusive for all types and sizes of investment coins.

The last non-destructive test to be described here is electrical resistivity testing. There is considerable merit in such testing because silver is known to have the lowest electrical resistivity of any of the elements in the periodic table of elements while copper and gold follow as a close second and third, respectively. Unfortunately, the resistance of silver, gold, copper and aluminum are all so low that quantitative values cannot be directly measured using commercially available Ohm-meters or electronic multi-meters. The equipment necessary to make a direct resistance measurement is too complex for casual users to operate and is more expensive than many casual investors who hold investment coins and bars are willing to pay. Further, this type of testing will be limited to only a specific surface area that is tested and the depth of testing is often limited by a factor known as the "skin-effect".

There are two distinctly different electromagnetic tests currently available that can be used to infer the electrical resistivity of an investment coin. Both of these tests are based on inducing electrical eddy currents within the metal coin's metallic volume. One test can be performed on a stationary coin by employing an electromagnet with a rapidly changing magnetic field while the other test requires relative motion between one or more permanent magnets and the test coin. This relative motion between the coin and permanent magnets induces eddy currents in localized regions of the test coin where the magnetic field is changing due to the motion. In one configuration, a small magnet is placed and released so that it slides down the face of a larger test coin that is inclined at an angle to the horizontal. In another configuration, a coin is placed and released at the top of an inclined plane formed by a series of rectangular magnets placed side-by-side.

In the latter case, the eddy currents first grow as the moving coin enters a magnetic field that is usually oriented normal to the coin's obverse and reverse surfaces. Then, the eddy currents diminish as the moving coin passes out of the magnetic field. It is well known that the lower the electrical resistivity (or, equivalently, the higher the electrical conductivity) of the coin's material, the greater will be the magnitude of the induced eddy currents. The net effect of the growth and decay of eddy currents as a coin passes by a permanent magnet is to convert a fraction of the coin's energy of motion into resistive electrical heating within the coin. And this causes the motion of the coin to slow down. If multiple permanent magnets are used in series, each one will cause a similar reduction in the coin's speed as it passes into and out of a sequence of magnetic fields associated with the multiple magnets.

This slowing-down effect is well known and has been used as the basis for validating silver coins and bars in coin-operated vending machines pre-1965 when United States dimes and quarter-dollar coins were made with material having 90% silver content. The coins inserted in a vending machine rolled down an inclined track past one or more permanent these magnets. If they were made of silver, they would be slowed down by the induced eddy current effect, described above, so that they could be subsequently identified and separated from counterfeit slugs that contained little or no silver and were not substantially slowed down.

Although high silver content coins are no longer produced in the United States for day-to-day financial transactions, a simple type of specialized equipment has recently been introduced using the eddy current effect to evaluate silver bullion coins such as the Silver American Eagle coins. This prior art apparatus is shown in FIG. 1, below. It consists of a relatively steep inclined plane (oriented approximately 50 degrees from horizontal) that is approximately 6 to 7 inches in height that is made from a group of closely spaced permanent rectangular bar magnets each 1/16 of an inch thick that form the surface of the smooth inclined plane. When a silver investment coin is place at the top of this inclined plane and is then released, the coin will slide downward noticeably slower than expected due to the eddy current effect. This slowing effect is relatively large in silver because of its high electrical conductivity as compared with other metals. Such a test allows one to reject counterfeit coins made of many different metal elements and metal alloys that will slide down the inclined plane substantially faster than silver, for example, zinc, nickel, etc. But some coins made out of other materials slide slower than silver. So, this test is more comprehensive than the simple magnet attraction test discussed above. However, this test is neither quantitative nor unambiguous in identifying counterfeit coins because there are a group of metals (excluding silver) that slide down an incline plane of permanent magnets with comparable or slower speeds than silver. This group includes copper, aluminum, and magnesium which are all common materials used to make coins. However, coins made from metals having substantially lower electrical conductivities, like zinc and tungsten, can be identified as being counterfeit. They slide down the inclined plane of magnets with very little resistance resulting in a velocity substantially greater then observed with a silver coin or bar.

In addition to the electrical conductivity testing described above using permanent magnets, eddy currents can also be induced using electromagnets that have time varying magnet fields. The benefit of this type of testing is that it is possible to make a quantitative measurements of the electrical conductivity of various coin and bar materials. One such testing unit, sold under the product name "Precious Metal Verifyer or PMV" (produced by Sigma Metalytics, see www.sigmametalytics.com), can be purchased for approximately $800. While the testing capability of the PMV can be useful, its manufacturer cautions in their product literature that "In order to make a bogus [counterfeit] coin appear correct [real] and have a correct [electrical conductivity] reading would be a significant undertaking, but not in principle impossible. So readings that are correct have to be taken as useful information, and not necessarily a guarantee of validity". Their literature goes on to say "There are known cases where common alloys can mimic the [electrical] resistivity of precious metal alloys". And an important example is given that "Johnson sandwich coins (modern US coins) have similar readings to gold". Here it should be explained that Johnson sandwich coins are US dimes, quarter, half-dollar and dollar coins introduced in 1965 after President Lyndon B. Johnson and his administration discontinued the traditional production of these coins from an alloy containing 90% silver. Johnson metal sandwich material has now been in continuous use for over 50 years. It has a copper core that is clad (sandwiched) between outer nickel layers. This material contains no gold or silver content at all, yet these coins still work in vending machines that were originally designed to detect 90% silver coins.

One of the shortcomings of producing eddy currents using variable magnetic fields to test metal coins and bars is that these fields may not fully penetrate the entire thickness of a test coin due to a well-known phenomenon often referred to as the skin-depth limitation. So, the measured electrical conductivity may be only that of the metal surface region nearest to the electromagnet probe and internally placed slugs of tungsten or other non-precious metals may be overlooked.

While the use of equipment such as the PMV and the other testing techniques discussed above can be used either singly or in combination, there is no assurance that they can be used to unambiguously discriminate pure gold and pure silver investment coins from counterfeit ones. Clearly there is a need for enhanced discrimination and preferably a method and associated equipment for absolute discrimination that could be used by those holding investment coins and bars to easily identity counterfeits. It would be particularly advantageous if this absolute method and associated equipment were inexpensive, portable, and required little or no specialized training to use. This would represent a welcome advance in the state-of-the-art of detecting counterfeit investment coins.

SUMMARY OF THE INVENTION

So, what other relatively simple non-destructive tests can be performed to discriminate against counterfeit coins and bars containing non-precious metals? And, significantly, is it possible that some limited combination of such tests could be used to unambiguously discriminate gold and silver investment coins and bars from all possible counterfeit ones? Although this is a very significant question, no record or reference could be found that it had ever been previously asked or answered. In fact, the answer to this question, as disclosed in this paper, is YES. Specifically, three simple independent tests are discussed below that have been determined to be sufficient for unambiguous discrimination of pure gold and pure silver investment coins and bars from counterfeit ones. The use of these tests on one or more coins and bars forms the basis of testing method referred to herein as the "1-2-3 Method" for testing the authenticity of gold and silver investment coins and bars. The three steps in this method are:
1. Measure the size (diameter and thickness of a test coin or outside linear dimensions of a test bar),
2. Measure the test coin's or test bar's weight, and
3. Compare the relative terminal velocity of the test coin or test bar moving down a magnetic slide to that of a known authentic coin or one with the same relative terminal velocity as an authentic coin (but, possibly, with different density).

The 1-2-3 Method relies on specific characteristics of pure gold and pure silver including very high electrical conductivity (electrical conductivity is reciprocally related to electrical resistivity) and relatively high (mass) density. Because the electrical conductivity of both pure gold and pure silver substantially diminishes if other metals are added to them to make an alloy, the 1-2-3 Method is limited to unambiguously discriminating pure gold and silver investment coins and bars from counterfeit ones. While the 1-2-3 Method can also be used on other precious metal coins and bars, such as platinum, palladium, and 22 karat (91.67% pure) gold coins to some limited advantage, the test results will not be unambiguous. Fortunately, as seen in Table 1, most gold investment coins are made out of pure gold and all silver investment coins are made out of pure silver. As a consequence, casual investors would be well advised to limit their future acquisitions to investment coins containing pure gold or pure silver if they plan to conduct their own validation testing using the 1-2-3 Method.

Two of the three tests in the 1-2-3 Method are conventional. The first one is that of measuring a coin's size with one of any number of well-known methods, including measurements of diameter and thickness employing a ruler, calipers, a physical template, or comparison with a similar coin known to be authentic, etc. The instructions made available to users of the 1-2-3 Method include specific published information on the diameters and thicknesses of all the popular gold and silver investment coins and bars. For example, the U.S. Government has published that the outside diameter of a Silver American Eagle coin is 40.60 mm and its thickness is 2.98 mm. Similar published information is available for all of the gold coins in Table 1 and all of the internationally produced silver investment coins, as well. Users of the 1-2-3 Method are encouraged to use calipers having a digital readout with sufficient accuracy to determine if measurements of the diameter and thickness made on a test coin or test bar are consistent with its published values. If so, the size test (Test 1) would be passed. Otherwise, counterfeiting would be indicated.

The second test requires measuring the weight of a coin using any one of a number of conventional weighing methods. The choices available range from using simple balance scales employing pre-calibrated weight standards (such as a known authentic coin of the same type being tested) on one arm to balance against a test coin on the other arm, to compact (pocket sized) electronic scales that can determine the weight of a coin to one one-thousandth of an ounce and are inexpensive to acquire. The speed, accuracy, and small size of electronic scales with digital output displays make them particularly convenient for use in counterfeit coin detection. Users of the 1-2-3 Method are encouraged to use such a scale for performing Test 2.

Test 3 in the 1-2-3 Method is a visual observation of the terminal velocity of a test coin relative to a known reference standard coin moving together down a slide or a quantitative measurement of the terminal velocity of a test coin moving down a magnetic slide. The magnitude of this relative terminal velocity has been found to be proportional to the electrical conductivity of the metal in a coin being tested. So, the third test is helpful in distinguishing gold and silver from other metals. This test requires the use of novel inexpensive magnetic slide apparatus that has been designed specifically to support the 1-2-3 Method. The equipment design will be described in detail in the DETAILED DESCRIPTION OF THE DRAWINGS, below.

Together, the use of all three tests in the 1-2-3 Method can provide unambiguous discrimination against counterfeit investment coins, as elaborated upon in the detailed discussion, below. Here, it is worth mentioning that the values of density (weight divided by volume of coin) and electrical conductivity (proportional to terminal velocity) that are derived from the 1-2-3 Method are bulk physical properties of the metal material in a coin or bar. As such, they are independent of the sizes and shapes of the coins and bars being evaluated. Further, since these are bulk characteristics of the material(s) in a coin or bar, they are not substantially influenced by any outer plating which would make up only a very small fraction of the total metal content in a coin or bar. However, the tests in the 1-2-3 Method are sensitive to internal voids, multiple cladding layers made from different metals, alternate metal plugs, cracks, and other defects often associated with counterfeit coins and bars.

BRIEF DESCRIPTION OF THE DRAWINGS

The above SUMMARY OF THE INVENTION as well as other features and advantages of the present invention will be more fully appreciated by reference to the following detailed descriptions of illustrative embodiments in accordance with the present invention when taken in conjunction with the accompanying drawings, wherein.

DETAILED DESCRIPTION OF THE DRAWINGS

Figure 1:
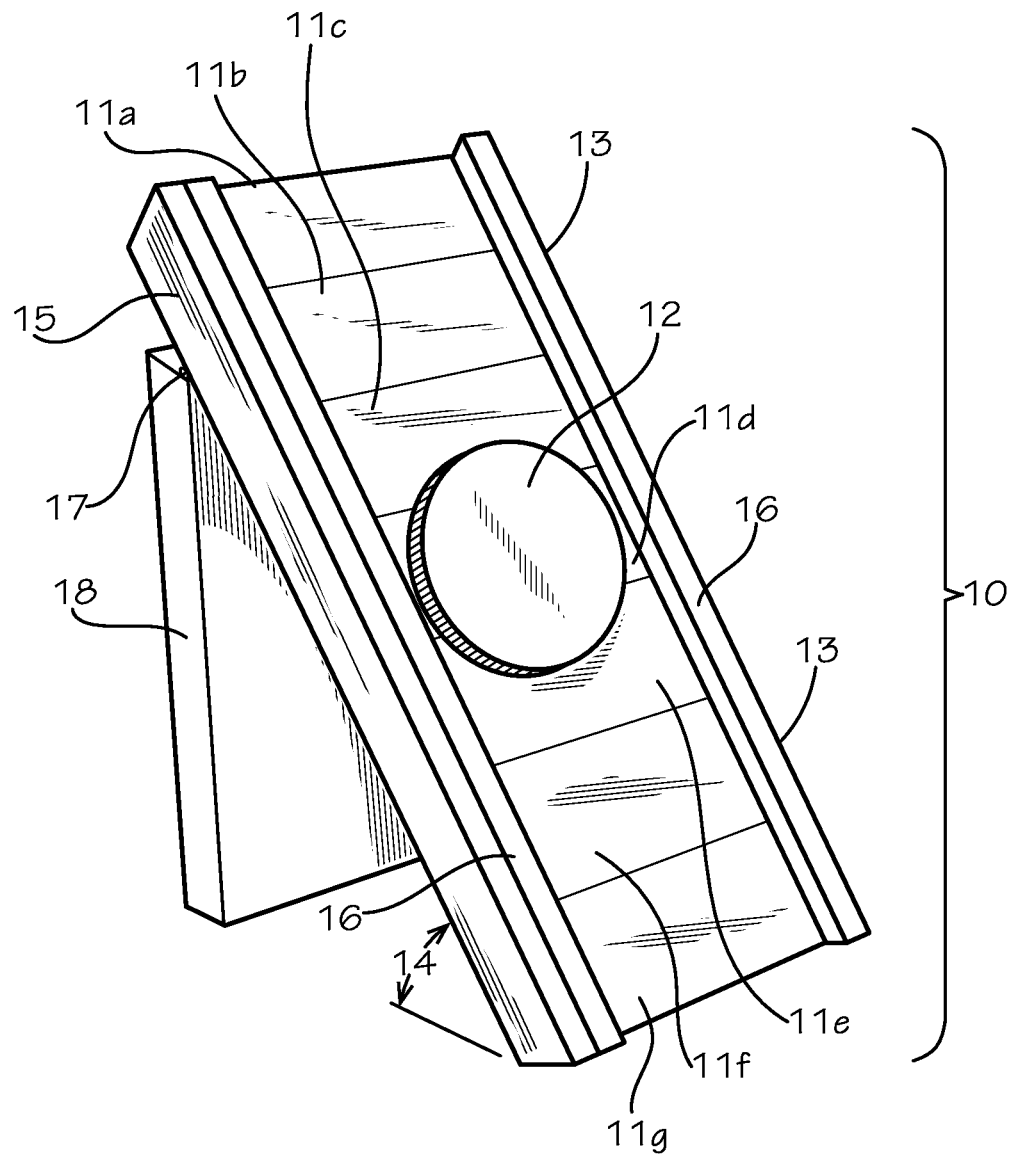
FIG. 1 is an isometric drawing of a prior art coin tester that employs a series of closely spaced permanent magnets to slow down a silver coin sliding down an inclined plane by magnetic drag.

FIG. 1 is a schematic diagram of a prior art silver coin tester 10 that employs a series of closely spaced permanent magnets 11a, 11b, 11c, . . . 11g to slow down a silver coin 12 sliding down an inclined plane 13 by magnetic drag caused by the induction of eddy currents in the silver coin. The inclined plane 13 is oriented at a slope angle 14 of approximately 50 degrees from horizontal and made from seven permanent magnets 11a, 11b, . . . 11g having alternating magnetic polarities oriented perpendicular to the inclined plane 13. These magnets are placed side-by-side and glued to a wooden substrate 15 to form a seven inch long inclined plane 13 that has rails 16 made of wood on both sides of the inclined plane to confine the coin or bar to the inclined plane. The inclined plane is connected to a wooden back support 18 by a hinge 17. This apparatus, that is appropriately called a "magnetic slide", was briefly described in the BACKGROUND OF THE INVENTION. It is commercially produced by Silver Click Media (928 Bridgewater Lane, Mesquite, Tex. 75181). Their web site (www.silvercoins.com) includes the following description of the operation of this product: The magnetic slide detects fake silver through an 'intrinsic property' known as diamagnetism. This produces an effect called the Eddy Current Brake [magnetic drag].

Each permanent magnet 11a, 11b, . . . 11g is two inches wide (in the horizontal direction), and one inch in length (in the down-hill direction) and $\frac{1}{16}$ inch thick. The width of the inclined plane 13 is sufficient to allow a single silver coin 12 the size of a one-Troy ounce Silver American Eagle (1.6 inches in diameter) to slide down the inclined plane 13 without concern for bumping into one of the two side rails 16 on the inclined plane 13. Since the slowing down of a pure silver coin, for which this silver coin tester was developed, can be visually discerned and differentiated from many but not all other counterfeit coin materials, this device can be used to perform a useful screening test of limited scope. For example, it can be used to differentiate pure silver coins by their slow sliding velocity down the inclined plane 13 of the silver coin tester 10 from faster sliding "fake" silver coins that contain only a limited percentage of silver, such as coins or bars made from zinc or nickel that may be plated with silver or that contain no silver at all, such as a U.S. penny (made from a zinc-copper alloy) or a nickel (made from a nickel-copper alloy). However, the silver coin tester would not be able to differentiate pure silver from a substantial number of metal alloys that could be prepared to match (equal) the sliding velocity of pure silver. An example of such an alloy would be an aluminum-nickel composition with the ratio of aluminum to nickel suitably adjusted to match the sliding velocity of pure silver.

Two other suppliers of magnetic slides were also found using an Internet search. All three suppliers employ similar high strength permanent magnets made from a commercially available neodymium-iron-boron composition (sometimes referred to as neodymium magnets or "super magnets"). And all of the magnets used in these various pieces of test equipment are two inches wide, presumably because this is a common and relatively inexpensive size and wide enough to comfortable fit a relatively large coin such as a 1-ounce Silver American Eagle (1.6 inches in diameter). These suppliers differentiate their products primarily by the quality of the wood and woodworking craftsmanship that goes into making the frame to support the inclined plane of magnets. One supplier uses an inexpensive composite wood material that is painted white. A second supplier has produced a much more finished appearing product having a maple wood frame that is varnished to preserve the natural beauty of the wood. The third supplier makes the support frame from expensive black walnut wood. The trend here appears to be to make and sell these magnetic slides as novelty items that purchasers could display on their desk and show off to friends—and also to occasionally check to see if their silver coins slide down the inclined plane noticeably slower than "fake silver". The novelty value of these coin testers comes from the unexpectedly slow motion of a relatively heavy silver coin down a reasonably steep slope. On first viewing, this motion tends to defy an observer's intuition.

Figure 2:
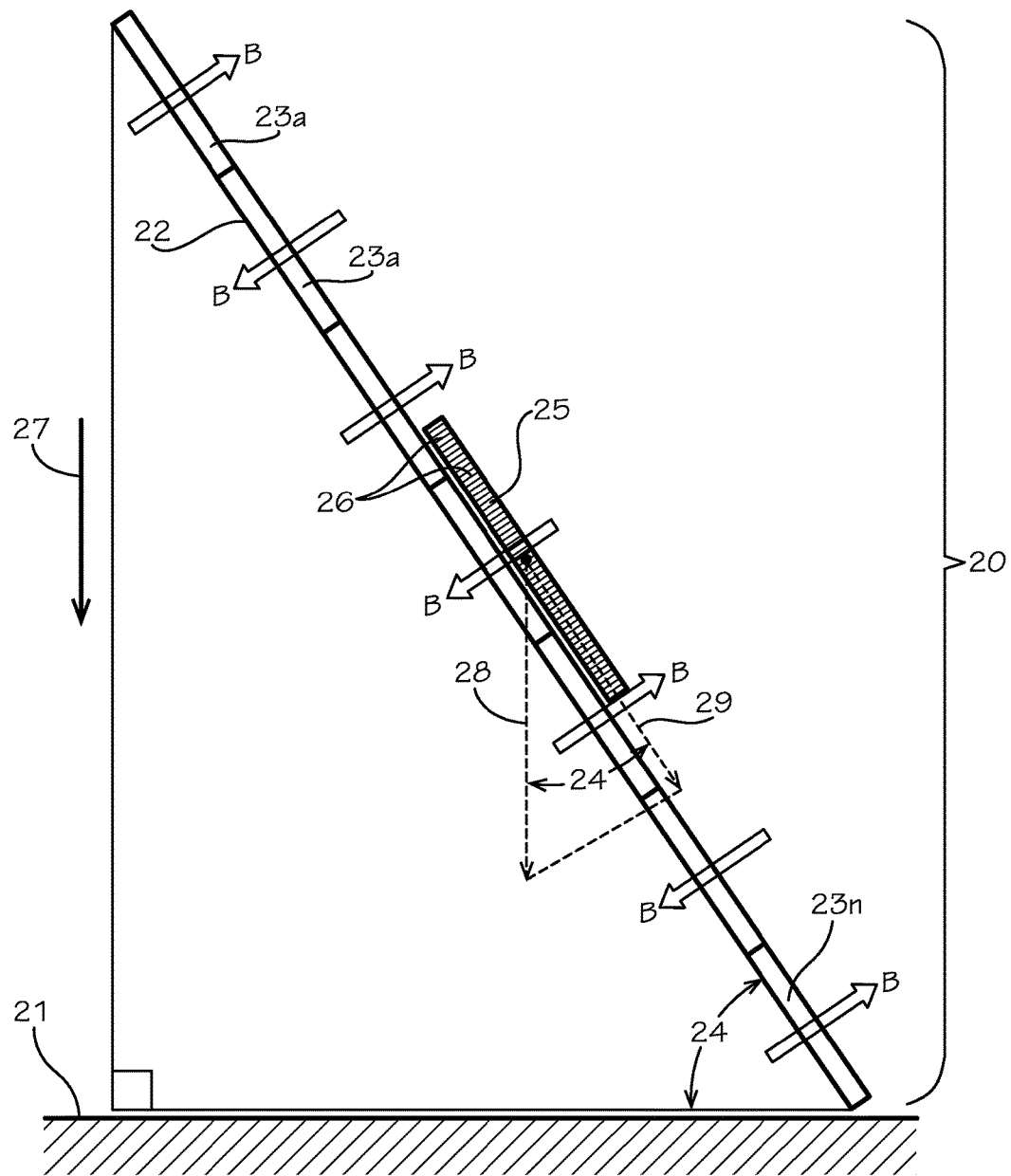
FIG. 2 is a side view drawing that shows the geometry used to support a quantitative engineering analysis of a magnetic slide coin and bar tester.

FIG. 2 is a side view drawing that shows the geometry used by the present inventor to support a quantitative engineering analysis of a magnetic slide. The objective of this analysis is to identify the engineering factors that determine the "magnetic breaking effect", which will subsequently be refer to as "magnetic drag", and to determine if the qualitative testing equipment described in FIG. 1 could, in some way, be refined to produce unambiguous and/or quantitative test results that would advance the art of counterfeit coin detection.

While this type of testing, by itself, was previously known to have some capability to discriminate silver coins from some other materials, such as nickel, and zinc, it was not realized that the use of a magnetic slide test along with a measurement of coin size and weight (the entire 1-2-3 Method) could serve to absolutely discriminate any authentic pure silver coin from a counterfeit one. This non-obvious result requires further explanation. However, before going on to the explanation, it is important to mention that an even more significant discovery was made. The same basic 1-2-3 Method for detecting counterfeit silver coins and bars can also be used to unambiguously discriminate pure gold coins and bars from counterfeit ones as well. This unanticipated additional capability is very significant to investors and important to this invention. So, the explanation that follows will be made applicable to both gold and silver.

A magnetic side structure 20 is shown resting on a flat horizontal surface 21. The inclined surface 22 is formed by a series of adjacent permanent magnet segments 23a, 23b, 23c, . . . 23n each with a magnet field of magnitude B directed perpendicular to the surface of the inclined plane but alternating in direction above and below the surface of the inclined pane between the said adjacent magnetic segments. The slope angle 24 between the inclined surface and the horizontal surface is also shown in this figure. In this side view drawing, the test coin 25 appears as a rectangular piece with closely spaced reed lines 26 shown on the circular edge of the coin 25. A vertical downward directed arrow 27, to the left of the magnetic slide structure, is a vector representing the acceleration of gravity, g. And force vector 28 represents the downward force acting on the coin having a mass, m. Based on elementary physics, the magnitude of this force vector, $F_g$, is the product of mass, m, and g. That is:

$$F_g = mg. \qquad (1)$$

The component of this force vector 29 in the direction down the magnetic slide can be determined by elementary geometry to be:

$$F_{g\theta} = mg \sin \theta. \qquad (2)$$

It is also well known the oppositely directed magnetic drag force, $F_M$, is $$F_M = (\text{constant})(\text{vol.})\sigma BV \qquad (3)$$

where B is the strength of the magnetic field, (vol.) is the volume of the coin 25, σ is the electrical conductivity of the coin's material, and V is the velocity of the coin 25. The constant in this equation is related to geometric factors, such as the down-hill widths of the magnet segments, that will discussed, below. Since there are no other forces acting on the coin, except a small frictional drag force which is negligible in comparison with the other forces, one can balance the forces on the coin 25 to get the relationship:

$$F_M = F_{g\theta} \qquad (4).$$

Then by substituting equations (2) and (3) into equation (4) and solving for V, one obtains:

$$V = mg \sin \theta / [(\text{constant})(\text{vol.})\sigma B] \qquad (5).$$

As a final step in this analysis, it is helpful to note that the mass, m of the coin 24 is equal to the product of its average density, ρ, and its volume (vol.). That is:

$$m = \rho(\text{vol.}) \qquad (6).$$

When equation (5) and (6) are combined, the (vol.) factors in the numerator and denominator cancel out, leaving the final result:

$$V = (\rho/\sigma)g \sin \theta / [(\text{constant})B] \qquad (7).$$

Importantly, the relative velocity of a coin on the magnetic slide has a fixed value that is proportional to the ratio of two parameters, p and a, that are basic properties of the coin's material:

$$V \sim (\rho/\sigma) \qquad (8)$$

and inversely proportional the magnetic strength, B:

$$V \sim B^{-1} \qquad (9).$$

This fixed velocity is referred to as the "relative terminal velocity". It should not be confused with free-fall velocity in the absence of drag.

Before concluding this discussion, it should be mention that the "constant" in equations (3) and (7) includes various factors such as the coefficient of sliding friction between a metallic coin and the magnetic slide. This coefficient of friction is approximately independent of the type of metal from which the coin is made. However, in order to protect valuable coins from scratches or other types of handling induced defects, it has been found that that the magnetic slide test may be performed with either an unprotected test coin or test bar or a protected test coin or bar that is placed inside of a thin protective plastic bag, envelope, or cover. However, the sliding coefficient of friction is usually increased for a coin with such plastic protection. So, when using a test coin that is protected by plastic, the reference coin should be similarly protected in order to obtain reliable and consistent test results.

From a practical viewpoint, equation (9) indicates that the relative terminal velocity is inversely proportional to the magnetic field strength B. Since a slow relative terminal velocity is helpful in reducing the overall size of a magnetic slide, it is advantageous to use super-magnets made from neodymium, Nd, iron, Fe, and boron, B, having the well-known chemical composition of $Nd_2Fe_{14}B$. Further, the thicker the magnets in the direction perpendicular to the plane of the magnetic slide, the stronger is it magnetic field. So, magnets having substantial thicknesses, in the range of 1/16 inch to 1/4 inch have been found to be preferred. In addition, the "constant" in equations (3) and (7) can be shown to be directly proportional to the down-hill width of the magnets that make up the magnetic slide. So that down-hill widths of 1/2-inch or less inch are preferred. But, down-hill widths less than 1/4-inch are difficult to handle during the assembly of a slide and they become increasingly fragile at smaller widths. So that down-hill magnet widths in the range of 1/4-inch to 1/2-inch are preferred. A typical magnetic side apparatus would have between 10 and 20 magnet segments in a single magnetic slide chute. If each magnet segment were 1/2-inch wide, in the down-hill direction, the total length of such a chute would be between 5 and 10 inches. It should be mentioned that the joints between adjacent magnet segments would form a series of visible down-hill grid lines with 1/2-inch spacing. Such grid lines can be helpful in assessing if there is a match between the relative terminal velocity of a test coin and a reference coin. For example, if there are 10 magnetic segments and the test coin and reference coin reach the bottom of the magnetic slide with a spacing of no more than a single 1/2-inch magnetic segment width after being simultaneously released from the top of the slide, one can infer that the relative terminal velocities of the test and reference coin are within 10% of each other.

Table 2 is a compilation of published densities, ρ, and electrical conductivities, σ, of various metals that are, or may be, significant to the production of coins and bars, both valid precious metal coins and bars and counterfeit ones. This table also includes a calculation of ratios, (ρ/σ), which is proportional to the terminal velocity, V, of a coin released on a magnetic slide. The final column on the far right hand side of Table 2 is a restatement of the terminal velocity, normalized so that the terminal velocity of pure silver is unity (1.0). The first entry in this table is silver because it has the highest electrical conductivity of any of the metal elements in the periodic table of elements. Subsequent entries of elements in the table are ordered based on declining electrical conductivity. In addition, there are a number of important alloys listed at the lower portion of this table.

TABLE 2

| Material | Denisty, ρ (gm/cm$^3$) | Electrical Conductivity, σ (×10$^6$ Siemens/meter) | (ρ/σ) (×10) | Relative Terminal Velocity |
|---|---|---|---|---|
| Elements: | | | | |
| Silver | 10.5 | 62.1 | 1.69 | 1.0 |
| Copper | 8.9 | 59.6 | 1.49 | 0.88 |
| Gold | 19.4 | 45.2 | 4.29 | 2.53 |
| Aluminum | 2.7 | 36.9 | 0.73 | 0.43 |
| Calcium | 1.55 | 28.2 | 0.55 | 0.32 |
| Beryllium | 1.85 | 25. | 0.74 | 0.44 |
| Magnesium | 1.74 | 23. | 0.75 | 0.44 |
| Rhodium | 12.4 | 22.3 | 5.56 | 3.29 |
| Iridium | 22.4 | 21. | 10.07 | 5.96 |
| Molybdenum | 10.2 | 18.7 | 5.46 | 3.32 |
| Zinc | 7.1 | 16.6 | 4.28 | 2.53 |
| Cobalt | 8.9 | 16.0 | 5.56 | 3.29 |
| Cadmium | 8.65 | 14.6 | 5.92 | 3.50 |
| Nickel | 8.8 | 14.3 | 6.15 | 3.64 |
| Ruthenium | 12.37 | 13.1 | 9.51 | 5.63 |
| Osmium | 22.4 | 12. | 18.7 | 11.17 |
| Indium | 7.31 | 12. | 6.09 | 3.60 |
| Lithium | 0.53 | 11.7 | 0.45 | 0.26 |
| Iron | 7.9 | 10.1 | 7.8 | 0.0* |
| Palladium | 12. | 9.5 | 12.6 | 7.46 |
| Platinum | 21.4 | 9.3 | 23.0 | 13.61 |
| Tungsten | 19.3 | 8.9 | 21.7 | 12.84 |
| Tin | 7.5 | 8.7 | 8.96 | 5.30 |
| Selenium | 4.79 | 8.35 | 5.74 | 3.40 |
| Tantalum | 16.65 | 8.06 | 20.65 | 12.2 |
| Strontium | 2.54 | 7.7 | 3.03 | 1.79 |
| Niobium | 8.57 | 7.66 | 11.2 | 6.62 |
| Rhenium | 21.02 | 5.6 | 37.5 | 22.2 |
| Chromium | 7.19 | 5.1 | 14.2 | 8.34 |
| Lead | 11.3 | 4.7 | 24.0 | 14.20 |
| Vanadium | 6.1 | 3.8 | 16.0 | 9.50 |
| Depleted Uranium | 20.2 | 3.4 | 59.4 | 35.15 |
| Antimony | 6.18 | 2.55 | 24.2 | 14.3 |
| Zirconium | 6.51 | 2.44 | 27.1 | 16.0 |
| Titanium | 4.5 | 2.4 | 18.75 | 11.09 |
| Selected Alloys: | | | | |
| 99% Au-1% Cu | 19.4 | 28.0 | 6.9 | 4.08 |
| 97% Au-3% Cu | 19.1 | 17.7 | 10.7 | 6.33 |
| 95% Au-5% Cu | 18.8 | 13.5 | 13.9 | 7.87 |
| 90% Au-10% Cu | 18.3 | 9.6 | 19.0 | 11.2 |
| 99% Au-1% Ag | 19.4 | 36.4 | 5.3 | 3.1 |
| 97% Au-3% Ag | 19.2 | 26.3 | 7.3 | 4.3 |
| 95% Au-5% Ag | 18.9 | 21.1 | 9.0 | 5.3 |
| 90% Au-10% Ag | 18.5 | 14.9 | 12.4 | 7.3 |
| 97% Ag-3% Cu | 10.4 | 52. | 2.0 | 1.18 |
| 95% Ag-5% Cu | 10.4 | 51. | 2.04 | 1.21 |
| 90% Ag-10% Cu | 10.3 | 50. | 2.06 | 1.22 |
| 95% Cu-5% Zn | 8.8 | 34.2 | 2.57 | 1.52 |

*Ferromagnetic -does not slide

There are a number of significant observations that can be made using this table. First, although silver has the highest electrical conductivity of any of the elements in the periodic table of elements, there are several other elements (aluminum, beryllium, magnesium, and copper) that exhibit lower (slower) magnetic terminal velocities, V. So, at first, it may not seem that the performance of silver on a magnetic slide is notable or special. The same appears true for gold.

The above observations concerning gold and silver would tend to suggest that it may not be possible to use their terminal velocity results obtained with a magnetic slide to discriminate pure gold and pure silver from other single metal elements or combinations of metal elements that might be bonded together (mechanically joined) or mixed together as alloys to make counterfeit coins and bars with matching terminal velocities. However, a conceptual breakthrough was made by reconsidering the data in Table 2 with regard to the following question: "Would it be possible for a counterfeiter to find an element or any combination of elements in the form of an alloy or composite structure that would have both a blended density and a blended terminal velocity that would match that of pure gold?" The non-obvious answer to this question is that no element in Table 2 or, in fact, in the entire periodic table of elements, has both a density and a terminal velocity that matches that of gold—or even comes close to such a match. And further, there is no blend of elements in any proportions that could match the density and terminal velocity of gold. To reach this conclusion requires some considerable effort to evaluate all possible elements with densities greater and less than that of gold that might be combined to match the density of gold and then go on to determine the terminal velocity of each such combination. This task is somewhat simplified because the rather high density of gold leaves only a limited number of elements for the higher density element component that could be used in such a counterfeiting blend (made by combining a higher density metal with a lower density metal in proper proportions to achieve the intermediate density of gold). The choices for higher density element components to use in such a counterfeiting attempt would be limited to platinum, rhenium, iridium, osmium and depleted uranium, as seen in Table 2 (excluding radioactive elements). And unfortunately for the counterfeiter, a careful analysis shows that there would be no viable choices for a second element of lower density that could be used to make a counterfeit material that would simultaneously match both the density and terminal velocity of gold. This is because all five of the above mentioned elements with higher densities than gold also have substantially higher terminal velocities than gold. The closest that a counterfeiter could come to a simultaneous match would be to select iridium as the base metal element with higher density and magnesium as the base element with lower density than gold. A density match to gold could be achieved with an alloy containing approximately 85% iridium and 15% magnesium. However, this combination would have a terminal velocity greater than 5.31 relative to that of silver (the relative standard in Table 2). There is just no possible way to reduce this this terminal velocity to match that of pure gold at 2.53 relative to silver (see Table 2). Such a substantial terminal velocity difference between pure gold and the iridium/magnesium counterfeit material would be easy to observe using a magnetic slide test. So, the counterfeiter would be out of business, at least in making counterfeit gold coins and bars that did not contain any gold, other than external gold plating, that would pass both a density and terminal velocity test.

However, if the counterfeiter were willing compromise and not attempt to replace all of the gold in counterfeit coin, he/she may think that there might be a chance of succeeding if he/she were to make a counterfeit coin out of an alloy containing, say, 97% gold and 3% silver. It is possible that the 3% silver replacement for gold may not make a recognizable difference to the measured density (19.4 authentic vs 19.2 counterfeit) when the size and weight of such a counterfeit coin were determined. And for the counterfeiter, making a 3% profit on a counterfeit coin, might be better than going out of business. However, to succeed, the counterfeiter would have to hope that the addition of 3% silver to the gold alloy would not make a significant change in the terminal velocity from that of pure gold because terminal velocity would be measured by Test 3 in the 1-2-3 Method. Such a hope would be a serious mistake because the addition of 3% (by weight) silver would increase the terminal velocity of the gold alloy by 70% (from 2.53 to 4.3, as can be seen in Table 2). In time, a smart counterfeiter would learn that any addition of a second metal to gold or any other elemental metal would substantially increase the terminal velocity of the alloy over that of the pure metal. This is a scientific truth that is known as the "alloy effect" which causes a decrease in the electrical conductivity of alloys due to increased scattering of conductive electrons from a random mixture of different sized atoms within an alloy. A more careful review of the selected alloys in Table 2 shows that the addition of copper to gold would have an even greater impact on its terminal velocity. A 3% (by weight) copper addition to pure gold would cause the terminal velocity of pure gold to increase by 150% (2.53 to 6.33 relative to silver, as seen in Table 2. The informative data on the electrical conductivity of alloys in Table 2 is from "Electrical Resistivity of Ten Selected Binary Alloy Systems" by C. H. Ho et al. (Journal of Physical Chemistry; Reference Data, Vol 12, No. 2, 1983)

Fortunately, a similar argument can also be made for silver coins and bars. It has been discovered that there is no single metal element or combination of elements that could be made that would simultaneously match both the density and relative terminal velocity of pure silver. Molybdenum comes very close to matching the density of silver (10.2 for molybdenum vs. 10.5 for silver), but silver has a much lower relative terminal velocity (1.0 for silver vs. 3.32 for molybdenum). So, a counterfeit molybdenum coin with silver plating would be easy to spot using a magnetic slide test. And adding a second element more dense than silver to molybdenum in order to produce an alloy with a density matching that of silver would simply increase the terminal velocity of the alloy over that of pure molybdenum.

Figure 3:
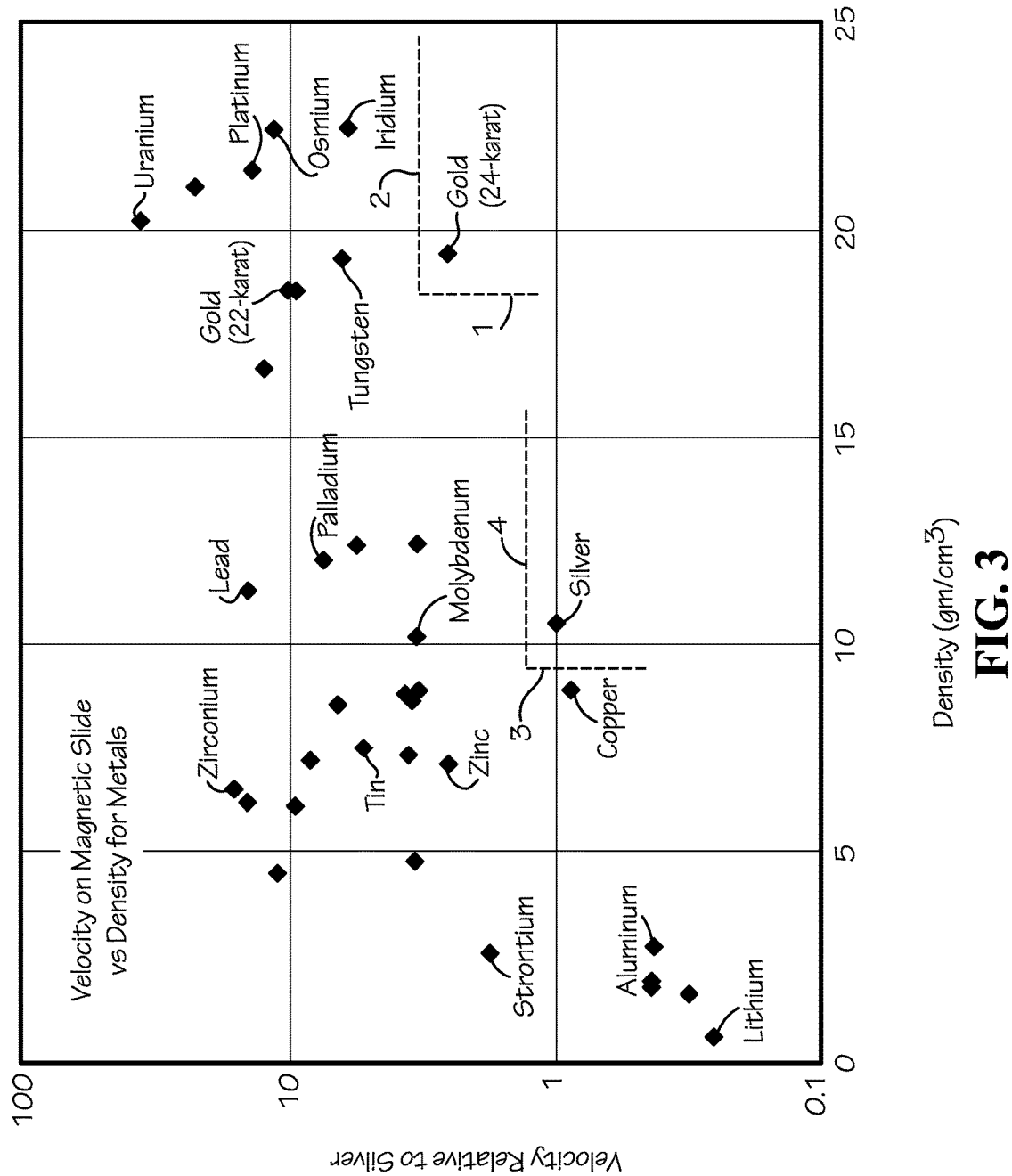
FIG. 3 is a graph showing the relative terminal velocity of various metallic elements on the ordinate and their density on the abscissa.

For purposes of this invention, it has been found that a helpful way to view the data Table 2 is to plot a graph, as in FIG. 3, showing the relative terminal velocities for pure elemental metals on the ordinate and their corresponding densities on the abscissa. There is a small black diamond shape for each metal. This is an inclusive graph for all non-magnetic metals in Table 2. But, only a fraction of them have been named in order to reduce clutter on the graph. One can see a clear trend showing that lower density metals (found in the lower left-hand corner of this graph) have low relative velocities. And as density of the metals increases, the trend is that their relative velocities also increase. What become evident when viewing this graph is that there are no elemental metals, other than pure 24-karat gold, that are located to the right of the vertical dotted line 1 and below the horizontal dotted line 2. So, if one were to find an elemental metal that is located in this zone, it must be 24-karat gold. Similarly, there are no metals, other than silver, that are located to the right of the vertical dotted line 3 and below the horizontal dotted line 4. So, if one were to find an elemental metal that is located in this zone, it must be pure silver. Although not obvious, the inventor has found that one would reach the same conclusion if not only elemental metals were included in this graph but all metal alloys and composite metal structures. For example, one can see using FIG. 3 that 22-karat gold (alloy) has a much higher velocity that pure gold (24-karat) due to the "alloy effect" that was discussed above. So, 22-karat gold would never be mistaken for pure gold.

The above discussion forms the basis of the inventive 1-2-3 Method for unambiguously discriminating pure gold and pure silver coins and bars from counterfeit ones. Recall, that the three steps in this method are:
 1. Measure the diameter and thickness of the test coin (or length, width and thickness of a test bar),
 2. Measure the coin's (or bar's) weight, and
 3. Compare the relative terminal velocity of the test coin (or test bar) to that of an authentic coin (or authentic bar) or one with the same relative terminal velocity as an authentic coin (or bar) but with different density.

The measurement results from Step 1 can be compared with values for diameters and thicknesses that are published for investment coins produced and distribute throughout the world or used to calculate the volume of the test coin [volume=$\eta/4$(diameter)$^2$×(thickness)]. The weight determined in step 2 can be compared to the published value for the coin under test. Then, steps 1 and 2 can be combined to determine the test coin's density (density=weight/volume). However, this calculation is not even necessary if the measured results of both steps 1 and 2 are consistent with published values for the coin under test (because the producer of the coin has already included foreknowledge of the proper density in the published values of size and weight). When taking into account the uncertainty in measurements, it has been found that there is a density match if the measured weight of the test coin is within 2% of its published value, the diameter is within 1% of its published value, and the thickness is within 5% of its published value and for test bars if the measured weight of a test bar is within 2% of its published value and its three outside linear dimensions are all within 2% of their published values. If the test coin or test bar has both the correct density and correct relative terminal velocity (measured in step 3), one can be assured that it is authentic. Otherwise, it is a counterfeit coin.

While measuring the size and weight of a test coin can be accomplished using conventional methods, measuring the magnetic terminal velocity requires enhancements to the qualitative magnetic slide testing device shown in FIG. 1 that will be discussed with the aid of FIG. 4, FIG. 5, FIG. 6, and FIG. 7.

Figure 4:
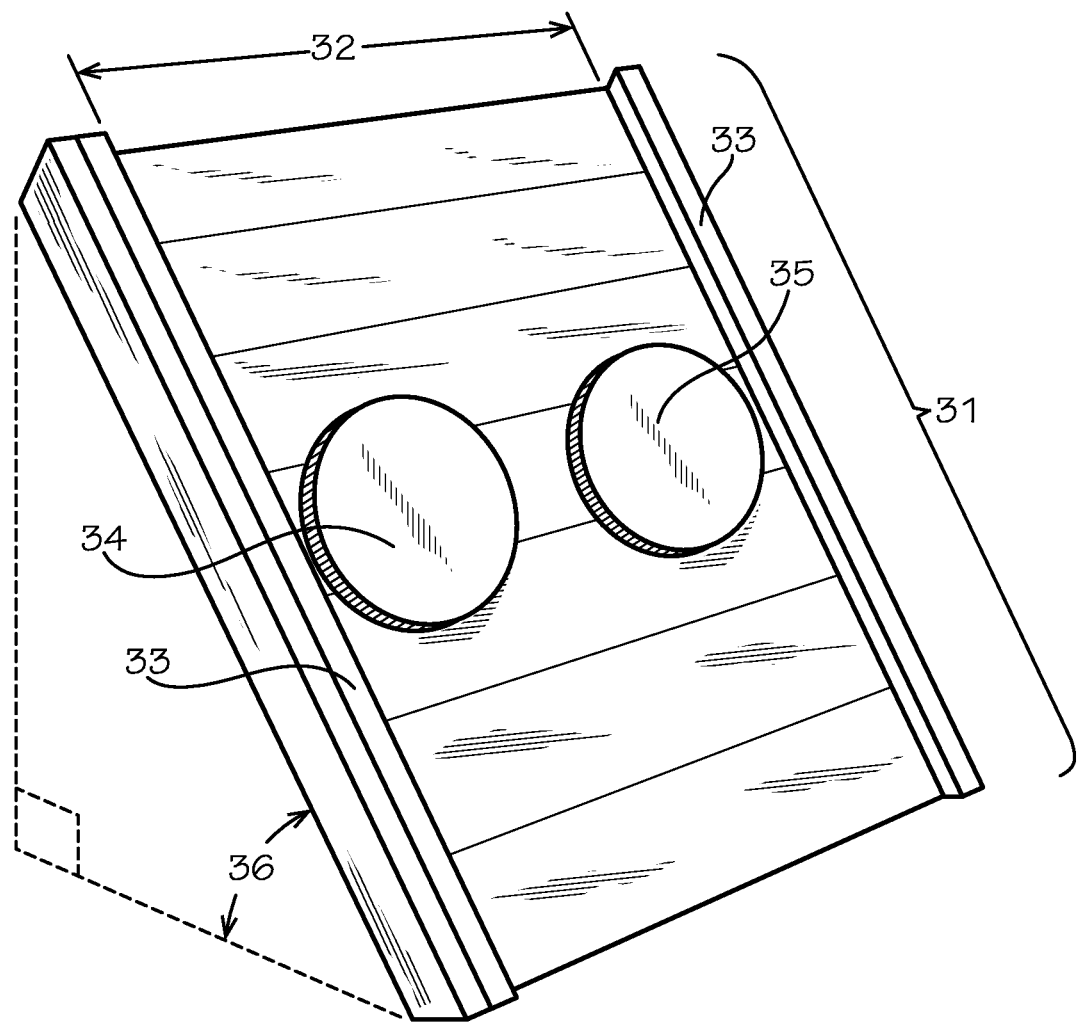
FIG. 4 is an isometric drawing of a magnetic slide coin and bar tester that has been modified to have an increased width so that two coins, one a test coin and the second a reference coin, may simultaneously slide down the inclined plane. This allows the user to make a quantitative comparison of the sliding velocities of the two coins (or a coin and a bar).

Before going further into the design details of the quantitative magnetic slide coin tester shown in FIG. 4, it is important to convey the full significance of the relative terminal velocities for various metals shown in Table 2 and how they can be used to assist an engineer in determining the slope angle, slope length, the number of magnets and their individual magnetic strengths. Central to this discussion is that the relative terminal velocities presented in Table 2 can only be realized when the magnetic drag force exceeds the acceleration due to gravity.

The concept of a terminal velocity is often discussed and applied to the motion of objects through a viscus medium. For example, if a glass marble and a steel ball bearing of the same size were dropped into a transparent container filled with a viscous oil such as cooking oil or glycerin, one would observe both objects falling downward at their respective terminal velocities. Anyone who has observed such a demonstration will recall that the terminal velocity of the steel ball bearing is greater than that of the glass marble because steel has a greater density than the marble. Both objects fall at different, but constant, velocities. On the other hand, if the marble and ball bearing were simultaneously dropped from the top of the Leaning Tower of Pizza, most everyone is aware that they would fall down not at a fixed velocity but with a continually increasing velocity due to the acceleration of gravity. And, of course, both the marble and ball bearing would hit the ground at the same time, as taught by Isaac Newton. One can connect the both the observation of a terminal velocity in the case of objects falling through a viscous liquid and free-fall of the same objects through air by considering the case of dropping both the marble and the ball bearing from the gondola of a hot air balloon located high above the ground. At first, both objects would undergo equal accelerations due to the force of gravity and they would fall side-by-side. As their velocities increase and eventually reach approximately 120 miles per hour, the drag caused by the low, but not negligible, viscosity of air would begin to set in. Both objects would reach their constant terminal velocities, with the ball bearing having a somewhat greater terminal velocity than the marble as they complete their fall towards earth. And the same effect would be observed if one were to replace the marble and ball bearing with a low density aluminum coin and a higher density lead coin (although both coins would tend to tumble as they fall due to the influence of turbulent air currents on their cylindrical shape).

The above description serves as a good analogy to explain how coins and bars move down a magnetic slide. The only difference is that the drag force on the coins and bars is due to magnetic field effects rather than viscosity. And many coins and bars have such low magnetic drag that they continue to accelerate in free-fall—never reaching their terminal velocities on a magnetic slide.

In a properly designed magnetic slide for authenticating gold and silver coins and bars, it is important that these coins and bars quickly reach their terminal velocities so that they can be observed to move down the slide similar to the way that the marble and ball bearing fall through cooking oil. This requires adjusting the strengths of the magnets used to form the slide, the slope angle of the inclined plane formed by a series of closely spaced magnets, and the linear dimension of the magnets in the down-slope direction.

Candidly, a practical coin authenticating device may not have been possible to construct before the advent of the very high strength "super magnets" made from a chemical composition of neodymium, iron, and boron ($Nd_2Fe_{14}B$). When properly selected and oriented, these high performance magnets can provide sufficient magnetic drag on both gold and silver coins and bars so that they quickly reach their terminal velocities.

FIG. 3 is a graph showing the relative terminal velocities of all non-magnetic metallic elements on the ordinate and their density on the abscissa. (NOTE: Magnetic elements, like iron, have zero velocity because they will stick in place on a magnetic slide rather than slide down-hill.) There is a diamond-shaped data point on this graph for each metal element, but only a fraction of these data points are named in order to reduce clutter on this graph. One can observe a general trend of increasing relative terminal velocity with increasing density. However, the data points for the various metals are scattered over a rather wide band from the lower left-hand side of the graph to the upper right-hand side of the graph with no predictable order. However, both gold and silver are located on the lower extremity of this rather wide band of data points. Of particular importance are the dotted lines 1 and 2 that are to the left and above the data point for pure (24-karat) gold, respectively, and for lines 3 and 4 that are to the left and above the data point for pure silver, respectively. With the aid of these dotted lines, one can visualize that there is no other metallic element with a density as great as gold that has as low a relative terminal velocity as gold. Further, there is no other metallic element with a density as great as silver that has as low a relative terminal velocity as silver. This important observation serves as a foundation for the 1-2-3 Method of testing for pure gold and pure silver coins and bars. However, fully establishing the 1-2-3 Method required far more analysis to verify that no possible metal alloys and composite metal structures can exist in the zones to the right and below dotted lines 1 and 2 for gold and to the right and below the dotted lines 3 and 4 for silver. But, that has been found to be the case.

FIG. 4 is a schematic diagram of a modified version of the magnetic slide tester shown in FIG. 1 that has an increased width 32 so that two coins (or one coin and one bar), one a test coin (or test bar) and the second, a reference coin, may slide down the inclined plane 31 starting from a side-by-side position at the top of the magnetic slide and being simultaneous released. This allows the user to make a quantitative visual comparison of the sliding velocities of the two coins. If both coins reach the bottom of the side at the same time, the test coins is thereby authenticated. But, if the test coin and reaches the bottom of the slide first, allowing for a 10% margin of uncertainty in the sliding velocity, it would thereby be categorized as counterfeit.

In this case, the width 32 of the inclined plane 31 between the two side rails 33 has been increased to accommodate two coins (or bars) placed side-by-side at the same elevation near the top of the incline. For example, a width of 3.5 inches or greater would accommodate two 1-oz American Silver Eagles coins that each have a diameter of 1.598 inches with an acceptable margin. One object is a test coin 34 or test bar (not shown) and the other is a reference coin 35 of pure gold or pure silver to match the expected material composition of the test coin or test bar. Alternatively, the reference coin could be made from some other metal alloy that had been selected to have a terminal velocity equal to the expected value for the coin under test assuming that this coin is authentic. The inclined plane 31 is oriented at an angle 36 from the horizontal with a support structure shown in this figure only by dotted lines but fully described in FIG. 7, below. A positive way to implement this testing in practice is to provide the user of the magnetic slide with a previously authenticated pure silver coin, such as a Silver American Eagle coin, that has a thin colored marking (e.g. an adhesive colored blue label or spot of blue paint) to be used as a reference when testing other silver coins. Use of color would avoid confusing the reference coin with the test coin.

And a pure gold coin, such as a Canadian Maple Leaf coin, that also has a thin color marking or adhesive label (e.g. red) could be used as a reference coin when testing pure gold. In view of the high value of such a pure gold reference coin, a satisfactory lower cost alternative would be to use a less expensive coin that has a similar terminal velocity to that of pure gold. In this regard, it has been found that a good choice would be a reference coin made from zinc. As can be seen in Table 2, zinc has a terminal velocity similar to gold and could therefore can serve as a useful reference coin even though its it could not pass the 1-2-3 Method because its density is substantially less than the density of gold. A U.S. penny (made from an alloy containing 97.5% zinc and 2.5% copper) has also been observed to be a reasonable reference coin for gold. The terminal velocity of a penny has been found to be slightly less than that of pure gold but it is still acceptable to serve as a reference for testing pure gold coins.

In order to accommodate two 1-ounce Silver America Eagle coins (each 1.6 inches in diameter) side-by-side on the magnetic side, the horizontal dimension of the magnets should be approximately 3.5 inches or greater. A dimension of 4.0 inches for the magnets would represent a preferred trade-off between realizing a reasonably comfortable side-by-side fit of two large coins on the same magnetic slide and the increased expense of using magnets larger than 4 inches.

Figure 5:
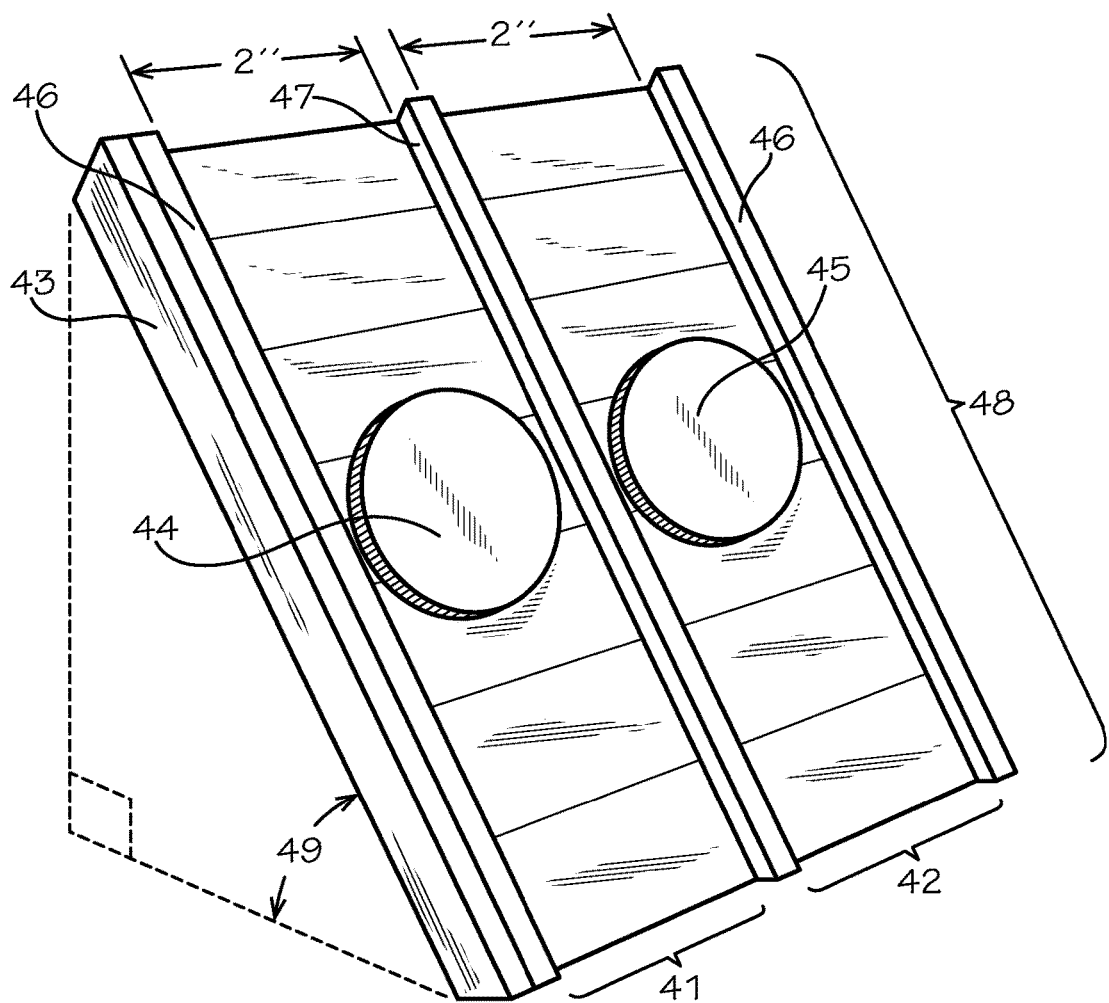
FIG. 5 is an isometric drawing of a magnetic slide coin and bar tester that has two adjacent and identical side-by-side magnetic slides on a common inclined plane with one slide to be used for a test coin and the second slide to be used for a reference coin.

FIG. 5 is an isometric drawing of an acceptable and likely lower cost alternative to the magnetic slide shown in FIG. 4. The magnetic slide apparatus in FIG. 5 has two side-by-side magnetic chutes, 41 and 42, each approximately 2 inches wide on a common back plate 43 (because the price of a typical 4-inch wide magnet is greater than the price of two 2-inch wide magnets) to form an inclined plane 48 oriented at an angle of 49 from horizontal. The test coin 44 or test bar (not sown) would be placed near the top of one magnetic chute and the reference coin 45 near the top of the other and then both coins would be simultaneously released. Each magnetic chute would have an outer side rail 46 (one on each side) and a common center rail 47 between the two slides to confine the coins or bar to their respective chutes. Orienting the magnetic field directions as indicated by the arrows labeled B for the individual magnets on the two chutes, as shown in FIG. 5, with horizontally adjacent magnets having oppositely directed magnetic fields has been found to result in a preferred magnetic slide structure that is more stable during assembly and service lifetime due to overall enhanced magnetic binding energy. After simultaneous release, if both coins reach the bottom of the slide at the same time (or nearly the same time), the test coin would be authenticated. Otherwise, it would be identified as counterfeit.

An alternative geometry for the magnetic slide coin tester, that is not preferred, would be to use a somewhat longer slope but retain the narrow 2-inch width of the magnetic slide. In this case, it would be possible to place the test coin close to but below the reference coin at the start of the test. If the gap between the coins or bars widens after the coins are simultaneously released and move down the magnetic side, the test coin could be identified as being counterfeit. The reason that this method is not preferred is that it requires considerably more hand-eye coordination to conduct such a test as compared with the side-by side testing.

Clearly, it would be desirable if a single magnetic slide could be used to authenticate both pure gold and pure silver coins and bars. In this regard, it is quite fortunate that both gold and silver have rather low terminal velocities (See Table 2) because many of the metals in Table 2 that have considerably higher terminal velocities would simply free-fall down the inclined plane because the strength of the magnetic drag on them is insufficient to balance the acceleration force due to gravity at high slope angles or overcome the frictional force that could cause the coins or bars to stop sliding at low slope angles. Of course, if the magnetic slide were made longer, even those metals with high terminal velocities would eventually reach their respective terminal velocities just as the marble and ball bearing dropped from the hot air balloon did in the discussion above. But, from a practical point of view, a magnetic slide capable of viewing the difference in terminal velocities of, say, tungsten and depleted uranium, two metals with rather high terminal velocities (see Table 2), would likely be taller than the ceiling height in most buildings. And there is no practical need for such a large structure.

Before leaving this point, it is interesting to speculate that the reason commercially available magnetic slides discussed in conjunction with FIG. 1, above, have been primarily dedicated to detecting "fake silver" is because silver has a lower terminal velocity than gold. This means that silver would require the least expensive magnets and the least sophisticated slide designs to observe the magnetic drag effect that causes the reduction in the terminal velocity of silver. Another reason for limiting the use of magnetic slides primarily to silver was noted in the course of reviewing recent Internet blogs for numismatists (coin collectors) and investors. When attempting to test a Gold American Eagle coin on a magnetic slide, like the one shown if FIG. 1 for silver testing, a contributor to the blog reported that it traveled very fast- as in free fall. While another blogger mentioned that gold just performed different from silver on a magnetic slide, neither of these bloggers was aware that the real reason for the observed high terminal velocity of the Gold American Eagle coin on the magnetic slide was because it is made out 0.9167 fine gold (22 karat) rather than 0.9999 fine gold (24 karat). Recall, that the "alloy effect" previously discussed in conjunction with FIG. 2 substantially reduces the electrical conductivity of the Gold American Eagle coins that are all made from 91.67% pure gold, 3% pure silver, and 5.33% copper and thereby substantially increases their terminal velocity relative to pure gold. It has been observed that the terminal velocity of gold Krugerrand coins (made from 91.67% gold and 8.33% copper) is somewhat greater than that of the American Gold Eagle coins.

It has been determined by further analysis of the data in Table 2 that the 1-2-3 Method for testing 22 karat (91.67% pure) gold coins and bars will not be absolutely definitive because it may be possible for future counterfeiters to make lower cost alloys that can simulate the densities and electrical conductivities of 22 karat gold and, thus, the performance of American Gold Eagles and Krugerrands on a magnetic slide. However, it is considered highly unlikely that any such counterfeit coins have yet been made because this specification is the first known disclosure that could provide guidance to counterfeiters. Further, the heavy metals required to make such possible counterfeits are relatively expensive (although not as expensive as gold) and are non-obvious. And because the American Gold Eagle and the Krugerrand are such popular investment coins, it is considered of some value to offer investors the capability to assess their current holdings of these coins using the 1-2-3 Method. In this regard, it has been discovered that reference coins can be made from alloys comprised of nickel, zinc, and copper that are suitable for simulating the performance of the 22 karat American Gold Eagle and Krugerrand coins on a magnetic slide. Due to the difference in composition of these two popular investment coins, different proportions of nickel, zinc, and copper are required to make two different metal alloys that can be formed into reference coins, one for testing American Gold Eagle coins and the other for testing Krugerrand coins on a magnetic slide. But neither reference coin will match the density of 22 karat gold. So they will not be confused with actual 22 karat gold.

Before leaving the discussion of testing of alternative metals using the 1-2-3 Method, it is relevant to include a brief discussion of the testing of pure platinum. The relevancy relates to the fact that platinum investment coins and bars are also produced by a number of countries that also produce gold and silver coins and bars. Unfortunately, platinum does not have a privileged position in the lowest portion of FIG. 3, like gold and silver. One can see that two other elements, osmium and iridium, both have somewhat higher densities and lower velocities than platinum. So, it would not be possible to make an absolute determination if a test coin or bar were made from platinum. Alloys of osmium and iridium could be used to match the velocity and density of platinum. However, it is likely that counterfeiters would avoid doing this because both osmium and iridium are comparably as expensive as platinum and melting osmium and iridium requires extremely high temperatures to form alloys. It seems highly unlikely that a counterfeiter would take on such an exceptional challenge as preparing an alloy of osmium or iridium with only a marginal financial gain.

One interesting effect that was clearly observed while developing magnetic slide for counterfeit detection is that coins or bars of identical metals usually have identical terminal velocities, as would be expected from the analysis presented with FIG. 2, above. However, it was noted that this expectation was not fully realized when coins having rather small diameters are being tested. Upon close observation one could see that the magnetic drag effect on a coin only occurs when the lower surface of the test coin is moving across at least one junction between two adjacent magnets, as expected based on the discussion in the BACKGROUND OF THE INVENTION. The initial development devices employed magnets that had a length of one inch in the down-slope direction, similar to the commercially available unit that was described above. So that when a larger coin, like the 1.6 inch diameter Silver American Eagle or a 1.2 inch diameter U.S. half dollar, were tested some portion of the lower surfaces of these coins was always be moving across a junction between two adjacent magnets and their motion down the inclined plane appeared to be uniform. However, when a U.S. dime was tested that has a 0.7 inch diameter, one observes a jerky motion. Every time the trailing edge of the dime moved completely past a junction of two adjacent magnets, the coin would lunge (jerk) forward (down-slope) with an observable acceleration until the leading edge of the dime reached the next junction between magnets causing a breaking action (drag). This observation proves a theoretical expectation that a uniform magnetic field (a zone where there are no junctions between magnets) should not cause any drag on a coin. Rather, the drag effect is caused entirely by a localized change in the magnetic field that is experienced by each localized area on the coin's surface as it passes a junction between adjacent but oppositely polarized magnets. A particularly negative consequence of the jerky motion of the dime is that its average terminal velocity is somewhat greater than expected based only on its metal content.

The solution to overcome the jerky motion of small test coins, like the U.S. dime or a $1/10$ Troy ounce gold coin, is to use shorter magnets that are, say, ½ inch or ¼ inch rather 1 inches in length (down-slope). As a general rule, it is preferred that the down-slope lengths of the magnets be less than the diameter of the smallest coin that might be tested.

Figure 6:
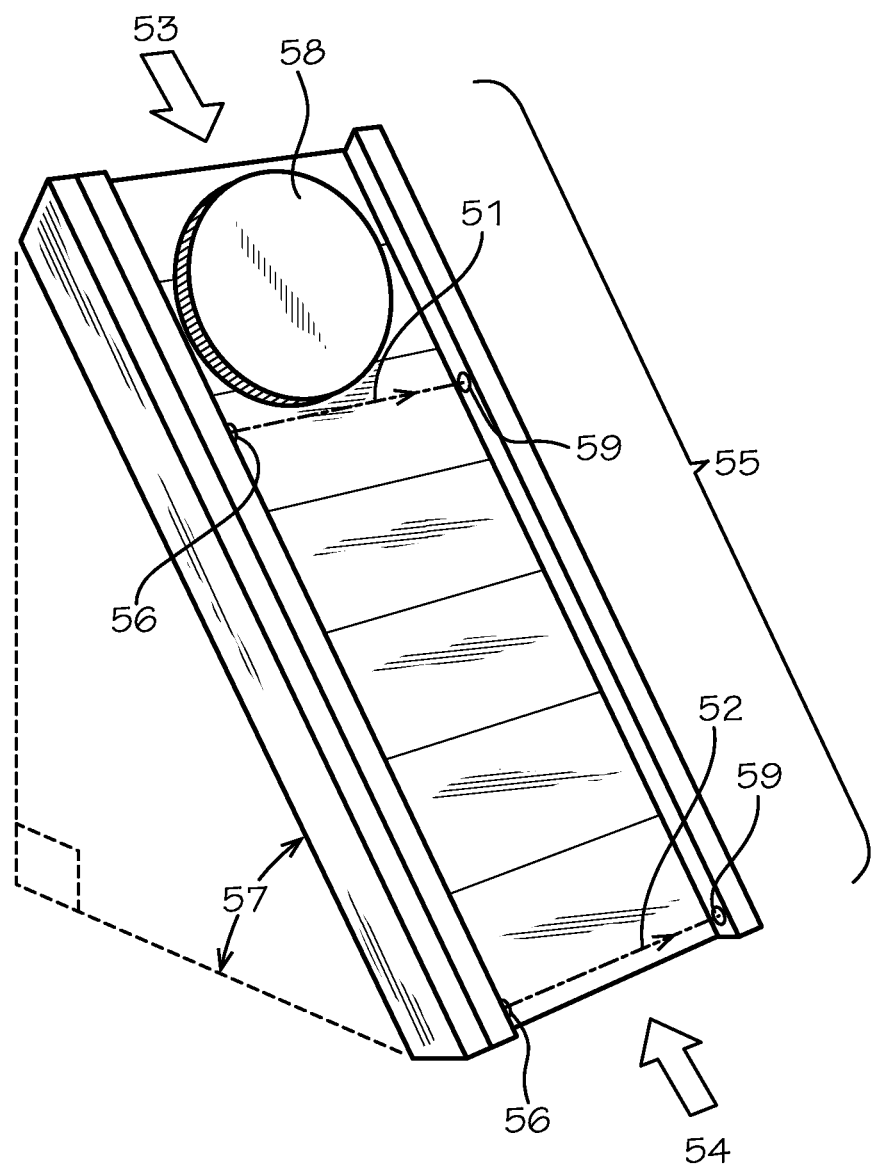
FIG. 6 is an isometric drawing of the magnetic slide coin and bar tester that has been modified with the addition of electro-optic features to automatically make a quantitative measurement of the coin's or bar's sliding velocity.

FIG. 6 is an isometric drawing of a modified version of the magnetic slide tester shown in FIG. 1. It has been modified with the addition of electro-optic features to make a quantitative measurement of a coin's magnetic slide velocity. The visual estimate of a coin's speed sliding down the inclined plane can be quantified by the addition of electronics and optics to measure the time of a coin's decent. The measurement is similar to that used to determine the time it takes for a skier to finish a down-hill race. Specifically, two horizontal light beams 51 and 52 are generated, one near the top 53 and the other near the bottom 54 of a magnetic slide inclined plane 55 oriented at an angle 57 from horizontal using a light source 56, for example, a light emitting diode (LED) or laser diode to produce each light beam 51 and 52. Then when a coin slides down the inclined plane 55 of magnets, these beams are sequentially interrupted by the passing of the leading edge of the coin 58 or bar (not shown). This interruption of each beam is detected using a photodetector 59 (for example, a silicon photodiode) and the coin's speed can be calculated in a straightforward manner by electronically determining the difference in the interruption times of the upper light beam 51 and the lower light beam 52 using a digital timing circuit (not shown) employing, for example, a reference quartz oscillator in conjunction with a microprocessor (not shown) that can subtract the upper beam's interruption time from that of the lower beam's interruption time. Since the distance between the upper and lower beams is known, this distance can be divided by the difference in interruption times to determine the coin's velocity of decent on the inclined plane of a magnetic slide. And since this distance is fixed, there is really no need to make a specific calculation of the coin's velocity. Rather, just the time difference between the interruption of the lower light beam 52 and upper light beam 51 is sufficient to characterize a test coin's relative terminal velocity.

Here, it should be mentioned that the location of the upper light beam 51 should be approximately ¼-inch to 1-inch below the start position of the coins or bars that are placed at the top of the slide in order to allow a reasonable distance for a released coin to reach its terminal velocity before interrupting the upper light beam 51.

When testing coins or bars using a magnetic slide as shown in FIG. 6, it is helpful to occasionally confirm its calibration by using a pure silver or pure gold coin that is known to be authentic to establish a reference terminal velocity for the next coin or bar or group of coins and bars that are going to be tested. Reference coins with terminal velocities equal to that or pure gold or pure silver may also be employed. This practice can compensate for minor changes in the orientation of the level surface on which the tester is placed. And it can also compensate for any contamination that might accumulate on the slope surface of the tester that could add to the drag on the test coin and thereby reduce its terminal velocity.

While the additional electronics for determining the interruption times between the upper and lower light beams can be include as part of this magnetic slide tester, it would be cost effective to use the electronics in the user's smart mobile telephone for this function. This could be accomplished by designing the magnetic slide tester simply to emit a brief acoustic tone (a short beep) when each of the light beams is interrupted. The tones corresponding to the upper and lower beam interruptions would then be detected (picked up) by the internal microphone in the smart phone and processed under the control of a custom application (App) developed for individuals using the 1-2-3 Method. This App could then be used to display on the phone's screen the difference in arrival times and/or a determination if the coin's speed was the correct value corresponding to either pure gold or pure silver.

Using a magnetic slide as in FIG. 6 to perform Test 3 in the 1-2-3 Method would be particularly useful if rapid coin and bar authentication were required to complete future financial transactions, including purchases and sales. In this case, it would also be helpful to more fully automate Tests 1 and 2 by using computer controlled optical scanning and recognition programs to assist in determining the size of a test coin or bar (Test 1) and automatically weighing the test coin or bar (Test 2).

Figure 7A:
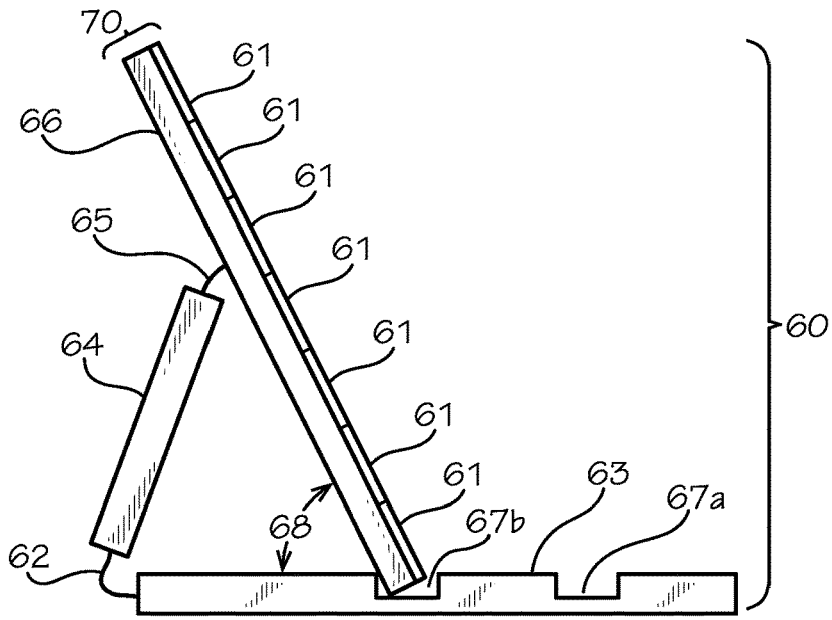
FIG. 7 shows the side view of an adjustable mechanical support structure for a magnetic slide coin and bar tester having an angle of inclination that can be altered to optimize testing of both gold and silver coins and bars.
Figure 7B:
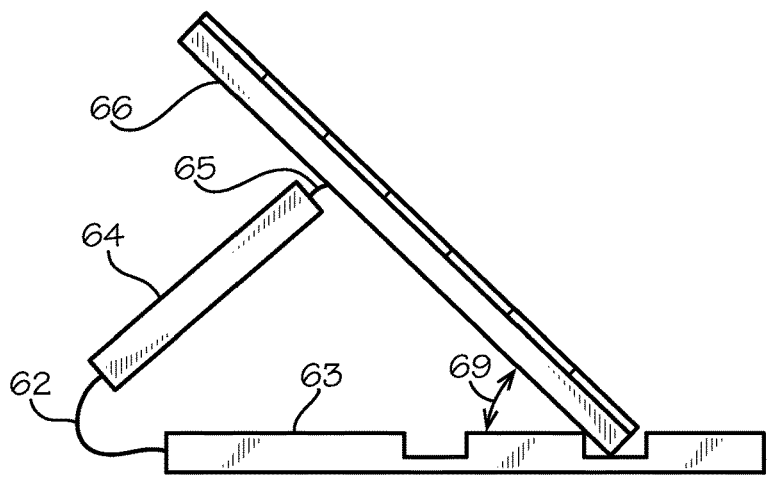

FIG. 7 shows the side view of an adjustable mechanical support structure 60 for a magnetic slide 70 having an angle of inclination that can be altered to optimize testing of both gold and silver coins and bars.

With regard to the design of magnetic slides, one of the important design factors is the slope angle of the inclined magnetic plane relative to the horizontal. By reducing this angle, one reduces the vector component of the gravitational force pulling the coin down the inclined plane (see FIG. 2). With less gravitational pull, the observed velocity of a coin is reduced. And while a reduced slope angle is helpful to view some coins and bars that would otherwise move too fast for optimal observation, a point is reached when the slope angle approaches approximately 30 degrees that normal friction between the coin and the surface of the inclined plane causes the coin to stop moving. At the opposite extreme, for very large slope angles, as the value reaches approximately 85 degrees, the test coin may topple over itself and free-fall down such a steep inclined plane. Slope angles between 30 degrees and 85 degrees are useful and a slope angle in the range of 40 to 80 degrees is preferred. The specific choice of a slope angle within this range is only a secondary consideration when using electro-optics to determine the tests coin's terminal velocity. Using a larger slope angle, corresponding to a higher observed velocity, has the advantage of reducing the test time. However, one must be careful to ensure that the faster moving gold coin has reached its terminal velocity rather than remaining in free-fall condition. If testing is conducted with a human observer, it can be helpful to allow the observer to select from two or more slope angles before starting to test a coin. For example, by selecting a slope angle of 40 degrees when testing gold coins and bars and 80 degrees when testing silver coins and bars, both coin types would slide down the magnetic slope at reasonably similar velocities. This is because the higher relative terminal velocity of gold as compared with silver (see Table 2) is mitigated by reducing the slope angle when testing gold coins or bars.

The support structure 60 shown in FIG. 7 for supporting a magnetic slide 61, is an example of a favorable design that could be used to easily orient the magnetic slide in two different positions; (a) with a relatively steep slope for testing silver coins and bars, and (b) a less steep slope for testing gold coins and bars. This support structure is similar in design to some folding plastic case structures that are employed to protect and support tablet computers. This type of structure typically has a flexible plastic hinge 62 joining the base plate 63 and the back plate 64 and another flexible plastic hinge 65 joining the back plate 64 to the slide support plate 66. Two (or more) permanent grooves 67a and 67b that are formed in the upper surface of the base plate 63 are used to engage and retain the slide support plate 66 in one of the two desired slope angle positions shown in views (a) and (b). Alternatively, two of more raised stops (not shown) formed or bonded onto the upper surface of the base plate could be used in lieu of grooves to accomplish the same function. The steeper slope angle 68 for testing silver is approximately 60 to 80 degrees from the horizontal and the less steep slope angle 69 for testing gold is approximately 40 degrees from the horizontal.

Another desirable feature for the support structure would be to provide a rotating joint between the back plate and the slide support plate that can be rotated through an angle of at least 90 degrees relative to the back plate of the support structure. Similar rotating joints are included in folding plastic case structures that are employed to protect and support tablet computers so that the user can view the screen either in a landscape or portrait mode. In the case of a magnetic slide support structure, such a rotational feature would allow for a longer slide to be used in the "portrait mode" or a shorter slide to be used in the "landscape mode".

Figure 7C:
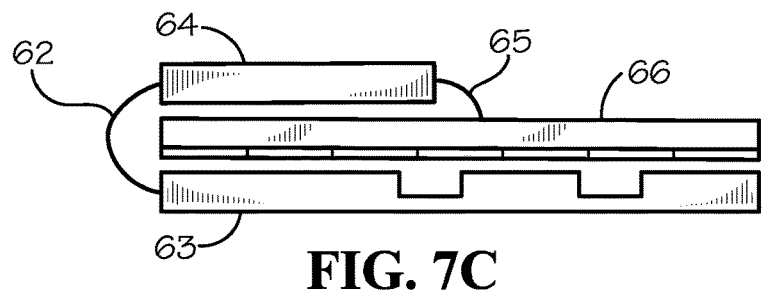

When not in use, the magnetic slide and its support structure can be folded flat as shown in FIG. 7(c).

In summary, a thorough analysis by the inventor of all possible elemental metals and metal alloy combinations has determined that that it would be impossible for a counterfeiter to produce a counterfeit pure gold or pure silver coin that could pass the 1-2-3 Method of testing described in this specification. This is an extremely important conclusion that may eliminate a significant barrier that impedes some investors from acquiring pure gold and pure silver investment coins. And this 1-2-3 Method may also enhance future commerce using pure gold and pure silver coins and bars as an exchange medium if, in the future, confidence were lost in paper monies. It should be recognized that the specific design details for a magnetic slide coin tester and its method of use discussed in this paper are only exemplary and should in no way serve to limit the broader scope of the magnetic slide coin tester or its methods of use, such as applying it to authentication of other metals such as 22 karat gold alloy coins and bars and pure platinum coins and bars.

The invention claimed is:

1. A method for determining if a test coin or test bar is made of pure gold or pure silver by first determining its density and its relative terminal sliding velocity on a magnetic slide apparatus and then concluding (1) that the test coin or bar is pure gold if its density corresponds to that of pure gold (19.4 gm/cm$^3$) and its relative terminal sliding velocity is no more than 2.53 (+10%) greater than the relative terminal sliding velocity of a pure silver coin or (2) the test coin or bar is pure silver if its density corresponds to that of pure silver (10.5 gm/cm$^3$) and its relative terminal sliding velocity is no more than 1.00 (+10%) greater than that of a pure a sliver coin or (3) the test coin or test bar is counterfeit (fake) if its density and/or its relative terminal sliding velocity does not match the above stated criteria for either pure gold or pure silver.

2. A method as in claim 1 in which the density of the said test coin or said test bar being evaluated is determined by conventional means, such as (1) using Archimedes' Method, or (2) by calculating density by dividing the measured weight of a test coin or test bar being evaluated by the measured volume of the test coin or test bar being evaluated, or (3) the density is inferred by comparing the measured weight, diameter and thickness of a test coin or the measured weight and the three outside linear dimensions of a test bar with known published values of these parameters for a pure gold or pure silver coin or bar of the type being evaluated and concluding that there is a density match if the measured weight of the test coin is within 2% of its published value, the diameter is within 1% of its published value, and the thickness is within 5% of its published value and for test bars if the measured weight of a test bar is within 2% of its published value and its three outside linear dimensions are all within 2% of their published values.

3. A method as in claim 1 in which the terminal sliding velocity down-hill on a magnetic side apparatus of a test coin or test bar being evaluated is visually compared to that of a reference coin that is simultaneously released on the same magnetic slide apparatus and a match in terminal sliding velocity is established if the relative terminal sliding velocity of the said test coin or said test bar moving down-hill on a magnetic slide is within 10% of the terminal sliding velocity of the said reference coin that is made from either pure gold or pure silver or some other metal having the same terminal velocity as an authentic pure gold or pure silver coin or bar of the type being tested (but, possibly, having a different density).

4. A method as in claim 1 for unambiguously discriminating a pure gold or a pure silver investment coin or bar from a counterfeit one by performing and passing all of the following three tests on a coin or bar being evaluated that together make up the 1-2-3 Method:

Test 1: a measurement of the size (diameter and effective thickness) of a coin being evaluated (test coin) or outside linear dimensions (length, width, and thickness) of a bar being evaluated (test bar), Test 2: a measurement of the said test coin's or said test bar's weight, Test 3: comparing the relative terminal sliding velocity of the said test coin or said test bar moving down-hill on a magnetic slide to that of a known authentic coin or bar of the type being tested or one having the same or substantially the same relative terminal velocity as an authentic coin or bar of the type being tested (but, possibly, having a different density), such that:

Test 1 is passed if the diameter is of the test coin is within 1% of its published value, and the thickness is within 5% of its published value and for a test bar its three outside linear dimensions are all within 2% of their published values, Test 2 is passed if the measured weight of the test coin is within 2% of its published value, Test 3 is (1) passed for a test gold coin or test gold bar if its relative terminal sliding velocity is no more than +10% greater than the terminal sliding velocity of a known pure gold coin or some other reference coin know to have a relative terminal sliding velocity equal to that of pure gold (but, possibly, having some other density than that of gold), (2) passed for a test silver coin or test silver bar if its relative terminal sliding velocity is no more than +10% greater than that of a pure a sliver coin.

5. The method as in claim 4 in which Test 1 is performed using calipers with an electronic digital read-out.

6. The method as in claim 4 in which Test 1 is performed using automatic optical recognition of the coin type and automatic measurement of the test coin's or test bar's size.

7. The method as in claim 4 in which Test 2 is performed using a commercial pocket sized weighing scale with a digital electronic read-out.

8. The method as in claim 4 in which Test 2 is performed using fully automated coin handling equipment and digital weighing of a test coin or test bar.

9. The method as in claim 4 in which Test 3 is performed with either an unprotected test coin or test bar or a protected test coin or bar that is placed inside of a thin protective plastic bag, envelope, or cover.

10. The method as in claim 4 in which Test 3 is performed using single magnetic slide (chute) having a width (orthogonal to the down-hill direction) of 3.5 inches or greater to accommodate both a reference coin and a test coin or bar side-by-side on an inclined plane with both the reference coin and the test coin or bar being simultaneously released at or near the top of the said magnetic slide and the said reference coin is known to have a relative terminal velocity equal or substantially equal to the expected relative terminal velocity of the test coin or test bar if it were authentic.

11. The method as in claim 4 in which Test 3 is performed using two identical side-by-side magnetic slides (chutes) on a common inclined plane with a test coin or test bar placed and released at or near the top of one of these magnetic slides (chutes) and a reference coin, known to have a relative terminal velocity equal or substantially equal to the expected relative terminal velocity of the test coin or bar if it were authentic, is placed at or near the top of the other magnetic slide (chute) and simultaneously released with the test coin.

12. A magnetic slide apparatus suitable for performing Test 3 in claim 4 consisting of two identical side-by-side and parallel magnetic slides (chutes) on a common rigid substrate to form an inclined plane which is made from two series of closely spaced and adjacent rectangular shaped permanent magnets of alternate magnetic polarities and the said two series of adjacent permanent magnets are bonded onto the said common rigid substrate to form an inclined plane oriented with a support structure that provides the said inclined plane with a slope angle between 30 degrees and 85 degrees from horizontal.

13. A magnetic slide apparatus as in claim 12 for which the magnetic field directions for horizontally adjacent magnets, one in each of the said two chutes, have oppositely directed magnetic fields.

14. A magnetic slide apparatus as in claim 13 in which the two magnetic chutes each have a single outside rail and a common central rail to constrain the motion of the coin(s) transverse to the down-hill direction.

15. A magnetic slide apparatus as described in claim 14 that employs one or more of the following reference coins;
(1) one that is either pure silver or has a relative terminal velocity that matches that of pure silver to within 5%,
(2) one that is either pure gold or has a relative terminal velocity that matches that of pure gold to within 5%,
(3) one that is an American Gold Eagle (22-karat) or has a relative terminal velocity that matches that of an authentic American Gold Eagle to within 5%,
(4) one that is a South African Krugerrand (22-karat) or has a relative terminal velocity that matches that of an authentic South African Krugerrand to within 5%, and
(5) one that is either pure platinum or has a relative terminal velocity that matches that of pure platinum within 5%, that can be distinguished from one another using thin color coatings, such as paints or an adhesive labels, and/or identification markings.

16. A magnetic slide apparatus as described in claim 15 that employs a reference coin when testing pure gold coins or bars that is made of zinc or a zinc alloy comprised of zinc and copper suitably adjusted so that the relative terminal sliding velocity of the reference coin is within 5% of that of a pure gold coin.

17. A magnetic slide apparatus as described in claim 12 having a series of magnet segments used to form the slide chutes that are made from neodymium, iron, and boron having the chemical composition $Nd_2Fe_{14}B$.

18. A magnetic slide apparatus as described in claim 17 having magnet segments such that each segment has a width in the down-hill direction of ¼-inch to ½-inch.

19. A magnetic slide apparatus as described in claim 12 having a series of magnet segments used to form the slide chutes that are each between ¹⁄₁₆-inch and ¼-inch thick (in a direction perpendicular to the surface of the magnetic slide).

20. A magnetic slide apparatus as described in claim 12 having a series of magnet segments that each have a length in the horizontal direction of 2-inches to 4-inches.

21. A magnetic slide apparatus a described in claim 12 in which the slope angle of the inclined plane can be adjusted by the user to a first larger slope angle optimized for testing pure silver and a second smaller slope angle optimized for testing pure gold.

22. A magnetic slide apparatus as described in claim 21 with a bottom plate having two or more notches or raised bars which can be used to constrain the motion of the bottom of the inclined plane to stabilize the entire coin testing structure at a desired slope angle.

23. A magnetic slide apparatus as described in claim 22 having a structure consisting of an inclined plane that can be rotated through an angle of at least 90 degrees relative to the back plate of the support structure and the said inclined plane and the said back plate are connected with a first hinge and a base plate and back plate are connected with a second hinge so that the entire structure can be collapsed flat for convenient storage.

24. A magnetic slide apparatus suitable for performing Test 3 of claim 4 that is made with a series of closely spaced permanent magnet segments of alternate magnetic polarity placed side-by-side to form an inclined plane oriented at an angle between 30 degrees and 85 degrees from horizontal down which a test coin can side with a relative terminal sliding velocity that is proportional to the difference between the times of interruption of two horizontally directed light beams, the first light beam being located at or near or at the top and second light beam being located at or near or at the bottom of the magnetic slide.

25. A magnetic slide apparatus as described in claim 24 in which the said light beams are produced by light emitting diodes (LEDs) or laser diodes and detected by photodetectors that are all secured to the substrate of the inclined plane.

26. A magnetic slide apparatus as described in claim 12 that employs one or more reference coins made from alloy(s) comprising nickel, zinc, and copper having chemical compositions selected to match or closely match the different relative terminal velocities of the American Gold Eagle and the 22-karat-gold South African Krugerrand coins on a magnetic slide.

\* \* \* \* \*